United States Patent
Dunlap et al.

[11] Patent Number: 6,114,327
[45] Date of Patent: Sep. 5, 2000

[54] ANTI-VIRAL COMPOUNDS

[75] Inventors: Steven Eugene Dunlap, Fishers; Louis Nickolaus Jungheim, Indianapolis; Mark Joseph Tebbe, Indianapolis; Gilbert Thomas Voy, Indianapolis; John Arnold Werner, Indianapolis, all of Ind.

[73] Assignee: Eli Lilly and Company, Indianapolis, Ind.

[21] Appl. No.: 09/425,093

[22] Filed: Oct. 22, 1999

Related U.S. Application Data

[63] Continuation of application No. PCT/US98/11214, Jun. 1, 1998.
[60] Provisional application No. 60/059,919, Sep. 24, 1997, and provisional application No. 60/048,607, Jun. 4, 1997.

[51] Int. Cl.[7] .................. A61K 31/4184; A61K 31/541; A61K 31/5377; C07D 235/30; C07D 417/04
[52] U.S. Cl. ..................... 514/227.2; 514/235.2; 514/322; 514/363; 514/370; 514/388; 544/54; 544/55; 544/139; 546/139; 548/137; 548/181; 548/304.7; 548/306.1
[58] Field of Search .................. 514/227.2, 388, 514/363, 370, 235.2, 320; 548/137, 304.7, 181, 308.1; 544/139, 54, 55; 546/199

[56] References Cited

U.S. PATENT DOCUMENTS

| | | | |
|---|---|---|---|
| 4,118,742 | 10/1978 | Paget et al. | 548/306 |
| 4,338,329 | 7/1982 | Paget et al. | 424/270 |
| 4,420,479 | 12/1983 | Morwick et al. | 424/246 |
| 4,434,288 | 2/1984 | Wikel, II et al. | 544/54 |
| 4,492,708 | 1/1985 | Spitzer | 424/273 |
| 5,545,653 | 8/1996 | Miller et al. | 514/388 |
| 5,693,661 | 12/1997 | Miller et al. | 514/388 |
| 5,821,242 | 10/1998 | Colacino et al. | 514/227.2 |
| 5,891,874 | 4/1999 | Colacino et al. | 514/234.5 |

FOREIGN PATENT DOCUMENTS

| | | |
|---|---|---|
| 0 047 122 | 8/1981 | European Pat. Off. |
| 58-188868 | 11/1983 | Japan |
| WO 97/46237 | 12/1997 | WIPO |
| PCT/US98/01030 | 1/1998 | WIPO |
| PCT/US98/07913 | 4/1998 | WIPO |
| PCT/US98/10299 | 5/1998 | WIPO |
| WO 98/55120 | 12/1998 | WIPO |

OTHER PUBLICATIONS

"Fields Virology, Third Ed.", B. N. Fields et al Eds., Lippincott–Raven, Philadelphia, p. 613, 614, 934, 935, & 940.

Encyclopedia of Virology, Academic Press, New York, p. 1115.

*Primary Examiner*—Mark L. Berch
*Assistant Examiner*—Thomas McKenzie
*Attorney, Agent, or Firm*—Arlene K. Musser

[57] ABSTRACT

The present application provides a series of benzimidazole compounds of formula I:

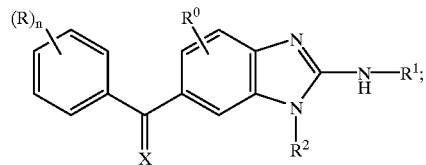

which inhibit the growth of picornaviruses, such as rhinoviruses (bovine and human), enteroviruses such as polioviruses, coxsackieviruses of the A and B groups, or echo virus, cardioviruses such as encephalomyocarditis (EMC), apthoviruses such as foot and mouth disease virus, and flaviviruses such as hepatitis C virus and bovine viral diarrhea virus.

Such compounds are also useful as intermediates for preparing additional benzimidazole antiviral compounds.

20 Claims, No Drawings

ANTI-VIRAL COMPOUNDS

This is a continuing application of International Application No. PCT/US98/11214, filed Jun. 1, 1998, which claims the benefit of U.S. Provisional Application Nos. 60/059,919, filed Sep. 24, 1997, and 60/048,607, filed Jun. 4, 1997.

FIELD OF THE INVENTION

The present invention relates to benzimidazole compounds and their use in inhibiting picornaviruses and flaviviruses.

BACKGROUND

The incidence of viral upper respiratory disease, the common cold, is immense. It has been estimated that nearly a billion cases annually appear in the United States alone. Rhinovirus, a member of the picornaviridae family, is the major cause of the common cold in humans. Because more than 110 strains of rhinoviruses have been identified, the development of a practical rhinovirus vaccine is not feasible, and chemotherapy appears to be the more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitis and myocarditis.

Illness related to rhinovirus infection is evidenced by nasal discharge and obstruction. Furthermore, it has been implicated in otitis media, predisposes the development of bronchitis, exacerbates sinusitis, and has been implicated in the precipitation of asthmatic altoclis. Although it is considered by many to be a mere nuisance, its frequent occurrence in otherwise healthy individuals and the resulting economic importance in terms of employee absenteeism and physician visits have made it the subject of extensive investigation.

The ability of chemical compounds to suppress the growth of viruses in vitro may be readily demonstrated using a virus plaque suppression test or a cytopathic effect test (CPE). Cf Siminoff, Applied Microbiology, 9(1), 66 (1961). Although a number of chemical compounds that inhibit picornaviruses such as rhinoviruses have been identified, many are unacceptable due to 1) limited spectrum of activity, 2) undesirable side effects or 3) inability to prevent infection or illness in animals or humans. See *Textbook of Human Virology*, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, antiviral benzimidazole compounds have been disclosed in U.S. Pat. Nos. 4,118,742 and 4,420,479.

In general, the compounds disclosed in the above patents do not have a desirable pharmacological profile for use in treating rhinoviral infections. Specifically, these compounds do not possess satisfactory oral bioavailability or a high enough inhibitory activity to compensate for their relatively low oral bioavailability to permit their widespread use. In addition, it is widely accepted in the art that compounds used to treat rhinoviral infections should be very safe from a toxicological standpoint. Furthermore, the processes disclosed in the above patents do not provide methods for the synthesis of some of the antiviral benzimidazoles with a high degree of stereochemical selectivity.

SUMMARY OF THE INVENTION

Accordingly, the present invention provides novel benzimidazole compounds which inhibit the growth of picornaviruses, such as rhinoviruses (bovine and human) and the like, enteroviruses such as polioviruses and the like, coxsackieviruses of the A and B groups, or echo virus, cardioviruses such as encephalomyocarditis (EMC) and the like, apthoviruses such as foot and mouth disease virus and the like, and flaviviruses such as hepatitis C virus, bovine viral diarrhea virus, and the like. In addition, the present invention provides a novel highly stereoselective method for preparing some of the novel benzimidazoles disclosed herein.

The present invention provides compounds of formula I:

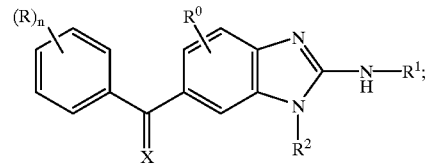

wherein:
n is 0, 1, 2, 3, 4 or 5;
R is independently at each occurrence hydroxy, thiol, halo, cyano, cyano($C_1$–$C_4$)alkyl, amino, halo($C_1$–$C_4$) alkyl, ($C_1$–$C_4$)alkylamino, di($C_1$–$C_4$)alkylamino, azido, carboxy, $C_1$–$C_6$ alkyl, $C_2$–$C_6$ alkenyl, carbamoyl, carbamoyloxy, carbamoylamino, N-($C_1$–$C_4$) alkylcarbamoyl, $OCF_3$, $OCCl_3$, $C_1$–$C_4$ alkoxy, $C_1$–$C_4$ alkoxycarbonyl, $C_1$–$C_4$ alkoxycarbonylamino, formyl, $C_2$–$C_4$ alkanoyl, formyloxy, $C_2$–$C_4$ alkanoyloxy, formylamino, $C_2$–$C_4$ alkanoylamino, $C_1$–$C_4$ alkylthio, $C_1$–$C_4$ alkylsulfinyl, $C_1$–$C_4$ alkylsulfonyl, pyrrolidino, piperidino or morpholino;
$R^0$ is hydrogen, halo, $C_1$–$C_4$ alkyl, or $C_1$–$C_4$ alkoxy;
$R^1$ is hydrogen, C(O)($C_1$–$C_6$ alkyl), $SO_2$($C_1$–$C_6$ alkyl), or C(O)$CF_3$;
$R^2$ is $C_1$–$C_6$ alkyl, $C_3$–$C_7$ cycloalkyl, halo($C_1$–$C_6$)alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, $SO_2R^3$, or a group of the formula:

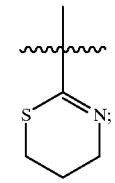

$R^3$ is $C_1$–$Cl_{10}$ alkyl, halo($C_1$–$C_6$)alkyl, $C_3$–$C_7$ cycloalkyl, substituted $C_3$–$C_7$ cycloalkyl, phenyl, substituted phenyl, naphthyl, thienyl, thiazolidinyl, furyl, pyrrolidino, piperidino, morpholino, or $NR^4R^5$;
$R^4$ and $R^5$ are independently $C_1$–$C_4$ alkyl or $R^4$ and $R^5$ taken together with the nitrogen atom to which they are attached form a pyrrolidino, piperidino or morpholino ring;
X is NOZ or CHY;
Y is $S(O)_mZ$, COZ, $CO_2Z$, or halo;
m is 0, 1, or 2;
Z is hydrogen or $C_1$–$C_{10}$ alkyl;
subject to the proviso that when Y is $S(O)_mZ$, $CO_2Z$, or halo, n can not be 0 or 1; or
a pharmaceutically acceptable salt thereof.

The present invention also provides pharmaceutical formulations comprising a compound of the present invention, or a pharmaceutically acceptable salt thereof, in combination with a pharmaceutically acceptable carrier, diluent, or excipient therefor.

The present invention further provides a method for inhibiting a picornavirus or a flavivirus, specifically a hepatitis C virus or a bovine viral diarrhea virus (BVDV), comprising administering to a host in need thereof, an effective amount of a compound of formula I, or a pharmaceutically acceptable salt thereof. The present invention also provides a process for stereoselectively preparing compounds of formula I where X is CHY and Y is halo where the halo atom is trans to the benzimidazole ring system.

DETAILED DESCRIPTION

The present invention relates to benzimidazole compounds of formula I, as described above, that are useful as antiviral agents.

Accordingly, one embodiment of the present invention is a compound of formula I, or a pharmaceutically acceptable salt thereof, for use in inhibiting a flavivirus.

A further embodiment of the present invention is a compound of formula I, or a pharmaceutically acceptable salt thereof, for use in inhibiting a picornavirus.

All temperatures stated herein are in degrees Celsius (° C.). All units of measurement employed herein are in weight units except for liquids which are in volume units.

The compounds of the invention can occur in either the cis or trans configuration. For the purposes of the present application, "cis" refers to those compounds where the moiety attached to the X group (—OZ or Y) is cis to the benzimidazole ring and "trans" refers to those compounds where the moiety attached to the X group is trans to the benzimidazole ring. Both isomers individually and mixtures thereof are included within the scope of this invention. The trans isomer is the preferred isomer.

Preferred compounds of this invention are those compounds of formula I(a):

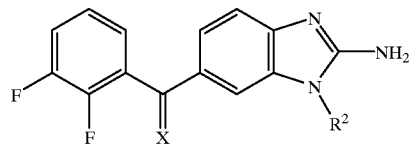

where:
n is 1, 2, 3, 4 or 5;
R is independently at each occurrence halo, $C_1$–$C_4$ alkyl, $C_1$–$C_4$ alkoxy or di($C_1$–$C_4$)alkylamino;
$R^0$ is hydrogen;
$R^1$ is hydrogen;
$R^2$ is $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino, morpholino or $SO_2R^3$;
$R^3$ is dimethylamino, $C_1$–$C_6$ alkyl, halo($C_1$–$C_6$)alkyl, $C_3$–$C_7$ cycloalkyl, substituted $C_3$–$C_7$ cycloalkyl; or a pharmaceutically acceptable salt thereof.

Of these preferred compounds, more preferred are those compounds of formula I where:
n is 2 or 3;
R is independently at each occurrence fluoro, methyl, ethyl, methoxy, ethoxy, dimethylamino;
$R^2$ is $C_1$–$C_4$ alkyl, $C_3$–$C_7$ cycloalkyl, pyrrolidino, or $SO_2R^3$;
$R^3$ is dimethylamino, $C_1$–$C_4$ alkyl, or $C_3$–$C_7$ cycloalkyl;
Z is hydrogen or $C_1$–$C_4$ alkyl;
or a pharmaceutically acceptable salt thereof.

Of these preferred compounds, more preferred are those compounds of formula I where:
R at each occurrence is fluoro;
$R^2$ is $C_1$–$C_4$ alkyl, $C_3$–$C_7$ cycloalkyl, or $SO_2R^3$;
$R^3$ is dimethylamino or $C_1$–$C_4$ alkyl;
Z is hydrogen or methyl;
or a pharmaceutically acceptable salt thereof.

Of these preferred compounds, the most preferred are those compounds of formula I(b):

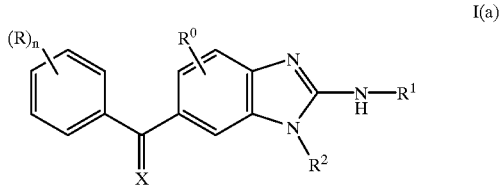

or a pharmaceutically acceptable salt thereof.

As used herein, the term "$C_1$–$C_{10}$ alkyl" denotes a methyl or ethyl group, or a straight or branched-chain saturated hydrocarbon of 3 to 10 carbon atoms of the formula $C_QH_{(2Q)+1}$, where Q is an integer from 3 to 10, that is attached to the parent molecular moiety at any point on the chain. Typical $C_1$–$C_{10}$ alkyl groups include, but are not limited to, methyl, ethyl, propyl, isopropyl, butyl, isobutyl, sec-butyl, t-butyl, pentyl, neo-pentyl, hexyl, 2-methylhexyl, heptyl, octyl, nonyl, decyl, and the like. The term "$C_1$–$C_{10}$ alkyl" includes within its definition the terms "$C_1$–$C_9$ alkyl", "$C_1$–$C_6$ alkyl", "$C_1$–$C_4$ alkyl", and "$C_3$–$C_6$ alkyl".

The term "$C_2$–$C_6$ alkenyl" represents a ethenyl group or a straight or branched chain hydrocarbon of three to six carbon atoms of the formula $C_QH_{(2Q')-1}$ where Q' is 3, 4, 5, or 6, that is attached to the parent molecular moiety at any point on the chain. Typical $C_2$–$C_6$ alkenyl groups include ethenyl, prop-1-enyl, isopropenyl, but-2-enyl, isobut-1-enyl, sec-but-2-enyl, pent-4-enyl, pent-1-enyl, hex-3-enyl, and the like.

The term "halo" and "halide" represent a chloro, fluoro, bromo, or iodo substituent that is attached to the parent molecular moiety.

The term "cyano($C_1$–$C_4$)alkyl" represents a $C_1$–$C_4$ alkyl group with a cyano moiety attached to the $C_1$–$C_4$ alkyl group. Typical cyano($C_1$–$C_4$)alkyl groups include cyanomethyl, 2-cyanoethyl, 1-cyanoisopropyl, 3-cyanopropyl, 3-cyanobutyl, cyano-t-butyl, and the like.

The term "halo($C_1$–$C_6$)alkyl" represents a $C_1$–$C_6$ alkyl group with 1, 2 or 3 halo atoms attached to the $C_1$–$C_6$ alkyl group. Typical halo($C_1$–$C_6$)alkyl groups include chloromethyl, 2-bromoethyl, 1-chloroisopropyl, 3-fluoropropyl, 3-bromobutyl, 3-chloroisobutyl, iodo-t-butyl, trichloromethyl, trifluoromethyl, 2-chloro-2-iodoethyl, 2,3-dibromopropyl, and the like. The term "halo($C_1$–$C_6$)alkyl" includes within its definition the term "halo($C_1$–$C_4$)alkyl".

The term "$C_1$–$C_4$ alkylamino" represents a straight or branched alkyl chain having from one to four carbon atoms attached to the parent molecular moiety through a nitrogen atom. Typical $C_1$–$C_4$ alkylamino groups include methylamino, ethylamino, propylamino, isopropylamino, butylamino, sec-butylamino, and the like.

The term "di($C_1$–$C_4$)alkylamino" represents two straight or branched alkyl chains having from one to four carbon atoms attached to the parent molecular moiety through a common nitrogen atom. Typical di($C_1$–$C_4$)alkylamino groups include dimethylamino, ethylmethylamino, methylpropylamino, ethylisopropylamino, butylmethylamino, sec-butylethylamino and the like.

The term "$C_1$–$C_4$ alkylthio" represents a straight or branched alkyl chain having from one to four carbon atoms attached to the parent molecular moiety through a sulfur atom. Typical $C_1$–$C_4$ alkylthio groups include methylthio, ethylthio, propylthio, isopropylthio, butylthio, and the like.

The term "$C_1$–$C_4$ alkylsulfinyl" represents a straight or branched alkyl chain having from one to four carbon atoms attached to the parent molecular moiety through a sulfinyl moiety. Typical $C_1$–$C_4$ alkylsulfinyl groups include methylsulfinyl, ethylsulfinyl, propyl-sulfinyl, isopropylsulfinyl, butylsulfinyl, and the like.

The term "$C_1$–$C_4$ alkylsulfonyl" represents a straight or branched alkyl chain having from one to four carbon atoms attached to the parent molecular moiety through a sulfonyl moiety. Typical $C_1$–$C_4$ alkylsulfonyl groups include methylsulfonyl, ethylsulfonyl, propylsulfonyl, isopropylsulfonyl, butylsulfonyl, and the like.

The term "$C_1$–$C_4$ alkoxy" refers to a straight or branched alkyl chain having from 1 to 4 carbon atoms attached to the parent molecular moiety through an oxygen atom. Typical $C_1$–$C_4$ alkoxy groups include methoxy, ethoxy, propoxy, isopropoxy, butoxy, and the like.

The term "$C_1$–$C_4$ alkoxycarbonyl" represents a straight or branched alkyl chain having from one to four carbon atoms attached to a carbonyl moiety through an oxygen atom wherein the carbonyl moiety is attached to the parent molecular moiety. Typical $C_1$–$C_4$ alkoxycarbonyl groups include methoxycarbonyl, ethoxycarbonyl, propoxycarbonyl, isopropoxycarbonyl, butoxycarbonyl, and the like.

The term "$C_1$–$C_4$ alkoxycarbonylamino" represents a $C_1$–$C_4$ alkoxycarbonyl group attached to the parent molecular moiety through a nitrogen atom. Typical $C_1$–$C_4$ alkoxycarbonylamino groups include methoxycarbonylamino, ethoxycarbonylamino, propoxycarbonylamino, isopropoxycarbonylamino, butoxycarbonylamino, and the like.

The term "N-($C_1$–$C_4$)alkylcarbamoyl" represents a straight or branched alkyl chain having from one to four carbon atoms attached to the nitrogen atom of a carbamoyl moiety wherein the N-($C_1$–$C_4$)alkylcarbamoyl group is attached to the parent molecular moiety through the oxygen atom of the carbamoyl moiety. Typical N-($C_1$–$C_4$) alkylcarbamoyl groups include N-methylcarbamoyl, N-ethylcarbamoyl, N-propylcarbamoyl, N-isopropylcarbamoyl, N-butylcarbamoyl, N-t-butylcarbamoyl, and the like.

The term "$C_2$–$C_4$ alkanoyl" represents a straight or branched alkyl chain having from one to three carbon atoms attached to the parent molecular moiety through a carbonyl moiety. Typical $C_2$–$C_4$ alkanoyl groups include ethanoyl, propanoyl, isopropanoyl, butanoyl, and the like.

The term "$C_2$–$C_4$ alkanoyloxy" represents a $C_2$–$C_4$ alkanoyl group attached to the parent molecular moiety through an oxygen atom. Typical $C_2$–$C_4$ alkanoyloxy groups include ethanoyloxy, propanoyloxy, isopropanoyloxy, butanoyloxy, and the like.

The term "$C_2$–$C_4$ alkanoylamino" represents a $C_2$–$C_4$ alkanoyl group attached to the parent molecular moiety through a nitrogen atom. Typical $C_2$–$C_4$ alkanoylamino groups include ethanoylamino, propanoylamino, isopropanoylamino, butanoylamino, and the like.

The term "substituted phenyl" represents a phenyl ring substituted with 1–5 substituents selected from the following: halo, cyano, $C_1$–$C_4$ alkyl, $C_1$–$C_4$ alkoxy, amino, or halo($C_1$–$C_4$)alkyl.

The term "$C_3$–$C_7$ cycloalkyl" represents a cyclopropyl, cyclobutyl, cyclopentyl, cyclohexyl, or cycloheptyl ring that is attached to the parent molecular moiety at any point on the ring.

The term "substituted $C_3$–$C_7$ cycloalkyl" represents a cycloalkyl ring substituted with 1–3 substituents selected from the following: halo, cyano, $C_1$–$C_4$ alkyl, $C_1$–$C_4$ alkoxy, amino, or halo($C_1$–$C_4$)alkyl.

The term "hydroxy protecting group" denotes a group commonly employed to block or protect the hydroxyl group while reactions are carried out on other functional groups of the compound. Examples of hydroxy protecting groups and methods for their installation and removal can be found in Chapter 2 of "Protective Groups in Organic Synthesis", 2nd Edition, T. H. Greene, et al., John Wiley & Sons, New York, 1991.

The term "carboxy protecting group" as used in this specification refers to one of the ester derivatives of the carboxylic acid group commonly employed to block or protect the carboxylic acid group while reactions are carried out on other functional groups of the compound. Carboxy protecting groups similar to those used in the cephalosporin, penicillin, and peptide arts can be used to protect a carboxy group in the compounds provided herein. Further examples of these groups are found in E.Haslam, "Protective Groups in Organic Chemistry", J. G. W. McOmie, Ed., Plenum Press, New York, N.Y., 1981, Chapter 5 and T. W. Greene, "Protective Groups in Organic Synthesis", John Wiley and Sons, New York, N.Y., 1991, Chapter 5.

The term "amino protecting group" as used in this specification refers to substituents of the amino group commonly employed to block or protect the amino functionality while reacting other functional groups on the compound. Amino protecting groups similar to those used in the cephalosporin, penicillin, and peptide arts can be used to protect an amino substituent of the compounds provided herein. Further examples of these groups are described by J. S. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1991, Chapter 7.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, ethanesulfonate, propanesulfonate, naphthalene-1-sulfonate, napththalene-2-sulfonate, mandelate, and the like.

The term "suitable solvent" refers to a solvent or mixture of solvents where the solvent or mixture of solvents employed is inert to the ongoing reaction and the reactants are sufficiently solubilized to effect the desired reaction.

The term "kinetic base" refers to a base which provides a non-reversible deprotonation of an acidic substrate and is reactive enough to effect the desired reaction without significantly effecting any undesired reactions. An example of an undesired reaction is the metal halogen exchange reaction. Examples of kinetic bases include, but are not limited to, metal amides such as lithium diisopropyl amide; metal alkoxides such as potassium t-butoxide; metal hydrides (e.g. sodium, lithium, or potassium hydride); primary alkyl lithiums such as methyl or n-butyl lithium; and phenyl lithium.

The term "lower alcohols" refers to methanol, ethanol, propanol, isopropanol, n-butanol, isobutanol, and t-butanol.

The term "halogenating reagent" refers to a reagent that can provide an electrophilic source of a halogen to the target molecule. Typical halogenating reagents include but are not limited to dibromobarbituric acid, N-bromo-, N-iodo-, and N-chloro succinimide, sulfuryl chloride, elemental chlorine, elemental bromine (and complexes of bromine such as bromine dioxane complex), elemental iodine, and interhalogen complexes such as Br—Cl, and I—Br, and the like. The term "brominating reagent" refers to the subset of halogenating reagents which delivers an electrophilic source of bromine to the target molecule. For further examples of halogenating reagents see R. C. Larock, Comprehensive Organic Transformations, VCH publishers, 321, 1989.

The compounds of formula I where X is CHY and Y is COZ may be prepared from compounds of formula II as represented in Scheme 1 below where n, R, $R^0$, $R^1$, $R^2$, and Z are as defined above and $Z^1$ is hydrogen or $C_1$–$C_9$ alkyl.

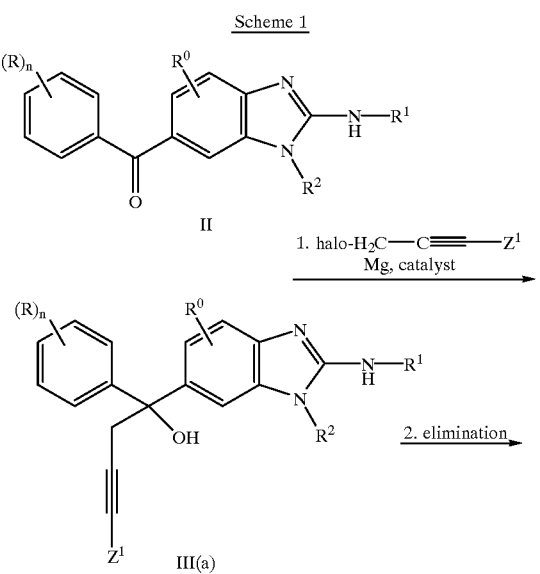

Scheme 1

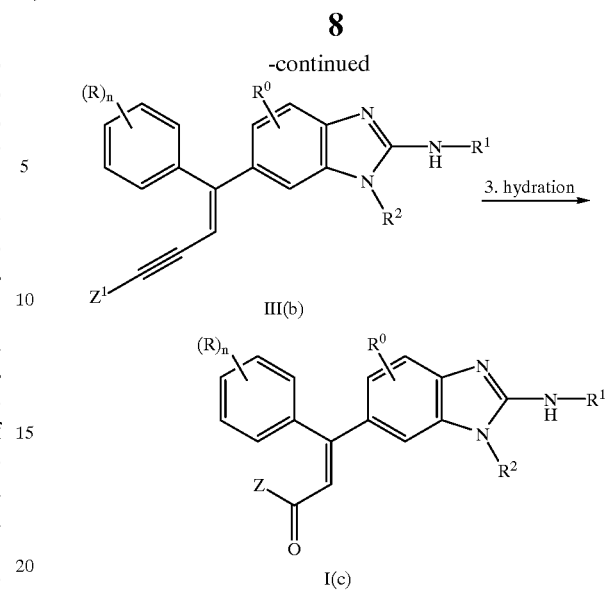

Reaction 1.1 may be carried out by preparing the Grignard reagent of an appropriately substituted acetylenic halide, preferably an acetylenic bromide, by dissolving the acetylenic bromide in the presence of magnesium and mercury (II) chloride in a mutually inert solvent. Once the Grignard reagent is formed it may be added to an appropriately substituted ketone of formula II to provide the corresponding acetylenic alcohol. The acetylenic halide is generally employed in a substantial molar excess, for example in from a three molar excess to about a ten molar excess relative to the compound of formula II, preferably in about a 5 molar excess. Typical solvents suitable for use in this reaction include any organic solvent such as diethyl ether or tetrahydrofuran. The reaction is generally substantially complete after about 1 to 24 hours when conducted at a temperature in the range of from about −40° C. to the reflux temperature of the reaction mixture. The reaction temperature is generally maintained at a temperature in the range of from about −5° C. to about 66° C. The reaction is preferably conducted under controlled reflux conditions for about 2 to 6 hours.

The acetylenic alcohol from reaction 1.1 above, may be eliminated to provide the vinyl acetylene benzimidazoles of formula III(b) which are then converted in a separate step to compounds of formula I(c). Preferably, compounds of formula III(a) may be eliminated and hydrated in one step to give the compounds of formula I(c) directly.

If it is desired to proceed in a step-wise fashion, compounds of formula III(b) may be prepared by activating the hydroxy moiety for elimination in the presence of a base such as tri($C_1$–$C_4$)alkylamine (e.g. triethylamine) or 4-dimethylaminopyridine (DMAP) in an aprotic solvent at a temperature of from about −100° C. to about 40° C. Typical activating agents include methanesulfonylchloride and trifluoromethanesulfonic anhydride. A preferred activating agent is methanesulfonylchloride. The activated compound is eliminated to provide the desired vinyl acetylene by gradually heating the reaction mixture. The activated compound is typically prepared in from about one to eighteen hours when initiated at −78° C. and allowed to progress at room temperature. Examples of solvents suitable for use in this reaction include methylene chloride, chloroform, tetrahydrofuran, and the like. The compounds of formula III(a) or III(b), prepared as described above may be converted to compounds of formula I(c). The reaction may be carried out by dissolving a compound of formula III(a) or III(b) in glacial acetic acid and concentrated sulfuric acid. Generally, an amount of acid sufficient to solubilize the compound of formula III(a) or III(b) is sufficient to effect the desired reaction. The volumetric ratio of acetic to sulfuric acid is generally about 20 to 1 and is preferably about 10 to 1. The reaction is generally carried out at about room temperature to the boiling point of the solvent but is preferably carried out at about 65° C. to 75° C. The compound of formula I(c) is typically prepared in from about one to eighteen hours when the reaction is performed at 70° C.

The compounds of formula I where X is N—OZ may be prepared from compounds of formula II as taught in U.S. Pat. No. 4,118,742, the teachings of which are herein incorporated by reference. For example, a compound of formula II, dissolved in a suitable solvent, may be treated with a compound of the formula Z—O—NH$_2$ in the presence of a base. Suitable solvents include lower alcohols, tetrahydrofuran, or dimethylformamide, and the like, but a preferred solvent is typically methanol. Suitable bases include, but are not limited to, carbonates, bicarbonates, and hydroxides (e.g. lithium, sodium, or potassium carbonate, bicarbonate, or hydroxide), and the like. A preferred base is pyridine. The compound of formula Z—O—NH$_2$ and the base are typically employed in a substantial molar excess relative to the compound of formula II. The reaction is typically conducted at about room temperature to the reflux temperature of the solvent.

The compounds of formula I where X is CHY and Y is S(O)$_m$Z or CO$_2$Z may be prepared from compounds of formula II as taught in U.S. Pat. No. 4,420,479, the teachings of which are herein incorporated by reference. For example, a ketone of formula II is reacted with a suitably substituted carbanion of the formula $^{-1}$CH$_2$CO$_2$Z or $^{-1}$CH$_2$SO$_m$Z, wherein Z and m are as defined above, to form the corresponding benzimidazole carbinol. The carbinol is then eliminated as described in Scheme 1, Reaction 2 above.

The requisite carbanions of the preceding paragraph are formed by reaction of a compound of the formula CH$_3$CO$_2$Z or CH$_3$SO$_m$Z with a strong base such as methyl lithium, n-butyl lithium, lithium diisopropylamide, potassium tert-butoxide, and the like. The compounds of formula CH$_3$CO$_2$Z or CH$_3$SO$_m$Z generally are reacted with about an equimolar quantity or an excess of strong base in an unreactive organic solvent such diethyl ether, tetrahydrofuran, dioxane, diglyme, methylene chloride, and the like. For example, dimethylsulfone can be reacted with a strong base such as n-butyl lithium in a solvent such as tetrahydrofuran to form the corresponding carbanion. Such reactions are typically carried out at a temperature of about –78° C. to about –50° C., and are substantially complete within about one to about six hours. Once the carbanion is formed, it typically is reacted in situ with a compound of formula II by simply adding the compound of formula II to the reaction mixture. The carbanion is generally utilized in an excess of about 1 to about a 10 molar excess relative to the compound of formula II, and the reaction is routinely carried out at a temperature of about –70° C. to about 30° C. The product of the reaction is the aforementioned carbinol benzimidazole, and can be isolated by simply acidifying the reaction mixture, for example with hydrochloric acid, and then removing the reaction solvent, for instance by evaporation under reduced pressure, but is preferably dehydrated in situ as described in Scheme 1, Reaction 2 above.

The compounds of formula I where X is CHY and Y is halo may also be prepared from compounds of formula II as described in U.S. Pat. No. 4,420,479. However, if the methods taught in U.S. Pat. No. 4,420,479 are followed, a trans to cis product mixture of at best 3:1 will result. Trans compounds of formula I where X is CHY and Y is halo may be prepared in a stereoselectively enhanced fashion by the novel process illustrated in Scheme 2 below where R' is R except R' does not include hydroxy, thiol, or C$_2$–C$_6$ alkenyl as substituents, and n, R$^0$, R$^1$, and R$^2$ are as defined above.

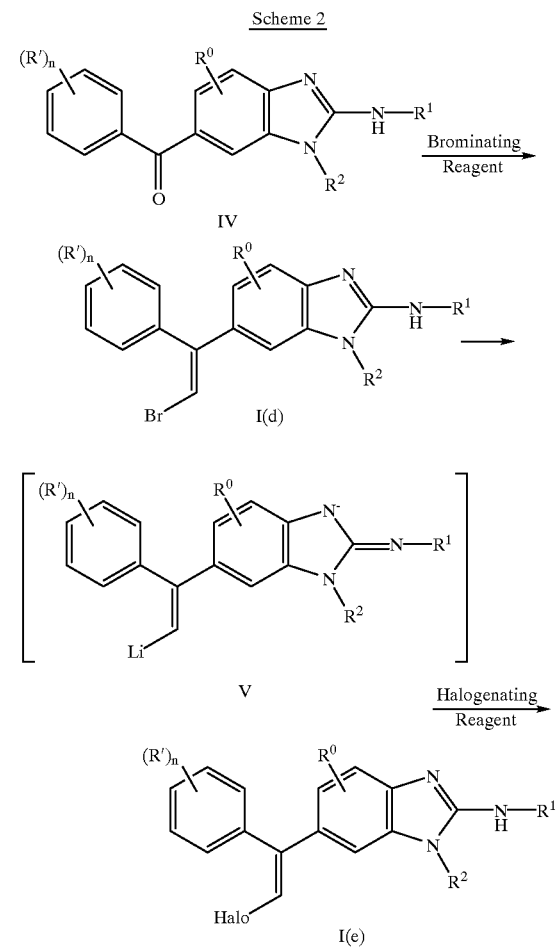

Bromination of compounds of formula IV, dissolved or suspended in a suitable solvent, as taught in U.S. Pat. No. 4,420,479 typically results in a trans to cis product ratio ranging from 67:33 to 75:25. Surprisingly, a slight excess of brominating agent and elevated reaction temperatures increases the initial yield of the desired trans isomer relative to the cis. About a 1.05 to about a 1.5 molar excess of brominating reagent, relative to the compound of formula IV, is generally required but about a 1.05 to 1.15 molar excess is typically preferred. It is also essential that the reaction be performed at a temperature above about 10° C., preferably between 20° C. and 30° C. Sufficient reaction times typically range between about 1 to 18 hours. The preferable reaction time is between 1.5 and 2.5 hours. Suitable reaction solvents include, but are not limited to, chloroform, methylene chloride, carbon tetrachloride, tetrahydofuran, mixtures thereof, and the like. A mixture of tetrahydrofuran and carbon tetrachloride is typically the preferred reaction solvent. If the bromination reaction is performed under the preferred conditions described above, surprisingly, the % of trans product in the isomeric mixture rises to between 85% and 91%. Furthermore, recrystallization affords an even further enriched mixture of the desired trans isomer. Solvents suitable for recrystallization include but are not limited to, carbon tetrachloride, tetrahydrofuran, ethyl acetate/hexane, lower alcohols such as ethanol and isopropanol, mixtures thereof, and the like. Acetonitrile was found to be the most efficient giving the trans isomer in >99% isomeric purity.

Compounds of formula I(d) may be converted to compounds of formula V by the well known metal-halogen exchange reaction. See e.g. "Organic Reactions", Chapter 7, R. G. Jones and H. Gilman, John Wiley & Sons, New York, 1951. The general conditions specific to the compounds of this invention for conducting a metal-halogen exchange reaction are to deprotonate a compound of formula I(d), dissolved in a suitable solvent, by treating with about 1 to 1.2, when $R^1$ is not hydrogen, or 2 to 2.5 equivalents of a kinetic base, when $R^1$ is hydrogen, at a temperature between about 0° C. and −120° C. In the case where $R^1$ is hydrogen, two equivalents of base are required to prevent simple protonation of the intermediate V upon metal-halogen exchange. Phenyllithium, is typically the preferred kinetic base. The deprotonation(s) with the kinetic base is (are) preferably performed at about −70° C.

About 1 to 2.5 equivalents of a 2° or 3° $C_3$–$C_6$ alkyl lithium, i.e. s-butyl lithium, isopropyl lithium, but preferably t-butyllithium, is then added to perform the metal-halogen exchange on the anion formed in the preceding paragraph. The metal halogen exchange is typically performed between −65° C. and −100° C., but the preferred temperature will depend on the number and type of R substituents in a compound of formula V. Generally, as the phenyl ring on the left hand side of the compound of formula V becomes more electron withdrawing, the preferred metal halogen exchange reaction temperature gets colder and approaches −100° C. For example, when the substitution pattern on the left hand ring is 2,5-difluoro, the preferred reaction temperature is about −100° C. However, when the substitution is 3-fluoro, the preferred reaction temperature is about −70° C. Once a compound of formula V is formed, it is not isolated but reacted in situ with a suitable halogenating reagent to provide the compounds of formula I(e). Chloroiodoethane is a preferred iodinating reagent. In order to carry out the metal-halogen reaction at temperatures approaching −120° C. without solidifying the reaction mixture, the "Trapp mixture" (4:4:1, THF:ether:pentane) is preferably used as the solvent. See Wakefield, B. J.; *Organolithium Methods*; Academic Press: San Diego, 1990; Section 2.2.1. When the reaction is run at higher temperatures, e.g. −65° C. to about −80° C., a preferred solvent is typically tetrahydrofuran.

The compounds of formula I where $R^1$ is $C(O)CF_3$, $C(O)$ ($C_1$–$C_6$ alkyl) or $SO_2(C_1$–$C_6$ alkyl), may be prepared by acylating or sulfonylating a compound of formula I, where $R^1$ is hydrogen, according to procedures known in the art. For example, the amine compound may be acylated with a suitable acyl halide, isocyanate or chloroformate, preferably in the presence of an acid scavenger such as a tertiary amine, preferably triethylamine. A preferred acylating agent is acetic anhydride. The reaction is typically carried out at a temperature of from about −20° C. to about 25° C. Typical solvents for this reaction include ethers and chlorinated hydrocarbons, preferably diethylether, chloroform or methylene chloride. The amine may be sulfonylated by reaction with a suitably substituted sulfonylating agent in an aprotic solvent. Typical sulfonylating agents include appropriately substituted sulfonyl halides or sulfonic acid anhydrides. A preferred sulfonylating agent is the sulfonyl chloride of the formula ($C_1$–$C_6$ alkyl)-$SO_2$—Cl. The reaction is typically carried out at a temperature from about −30° C. to about 50° C. in an aprotic solvent such as tetrahydrofuran or methylene chloride. The amine reactant is generally employed in equimolar proportions relative to the acylating or sulfonylating reactant, and the reaction is preferably performed in the presence of equimolar quantities of an acid scavenger such as a tertiary amine. A preferred acid scavenger for this reaction is N-methylmorpholine (NMM) or pyridine. Alternatively, the compound of formula I may be prepared using a ketone of formula II that has been acylated or sulfonylated using this procedure. When X is CHY and Y is halo, it is preferred that the acylation or sulfonylation be performed on a compound of formula I.

Mixtures of cis and trans compounds of formula I or vinyl acetylenes of formula III(a) may be isolated and the resulting cis/trans isomers separated using procedures known in the art. For example, the cis and trans forms may be separated using column chromatography, e.g. reverse phase HPLC. The compounds may be eluted from the column using an appropriate ratio of acetonitrile and water or methanol and water. The cis form of the compound may be converted to a cis/trans mixture by exposure to hu irradiation and recycled through the above-mentioned purification process. As described previously, chromatography and/or photochemistry are not necessary to prepare trans compounds of formula I where X is CHY and Y is halo. If the novel process described in Scheme 2 is followed, a simple recrystallization is all that is necessary to provide these trans compounds in greater than 95% isomeric impurity.

Generally, cis and trans compounds of formula III(a) separated in this way may be converted to their corresponding cis and trans compounds of formula I(c) without isomerization of the alkene moiety. In addition, this separation may be performed before or after conversion of compounds of formula I where $R^1$ is amino to compounds of formula I where $R^1$ is a C(O) ($C_1$–$C_6$ alkyl), $SO_2(C_1$–$C_6$ alkyl), or a $C(O)CF_3$ group. These transformations of the Rgroup will generally not effect an isomerization of the alkene moiety.

The pharmaceutically acceptable salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as methylene chloride for base addition salts. The salts normally precipitate out of solution within about one hour to about ten days and can be isolated by filtration or other conventional methods. For further instruction, see e.g. Berge, S. M, Bighley, L. D., and Monkhouse, D. C., *J. Pharm. Sci.*, 66, 1, 1977.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutically acceptable acid addition salts are those formed with mineral acids such as hydrochloric acid and sulfuric acid, and those formed with organic acids such as maleic acid, tartaric acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The ketone intermediates of formula II used in the above reactions may be prepared as detailed in the art. For example, the compounds of formula II where $R^2$ is $SO_2R^3$ may be prepared as shown in Scheme 3 where L is cyano or $CO_2R'$, $R'$ is $C_1$–$C_4$ alkyl, $L'$ is halo, and n, R, $R^0$, $R^1$, $R^2$, and $R^3$ are as defined above.

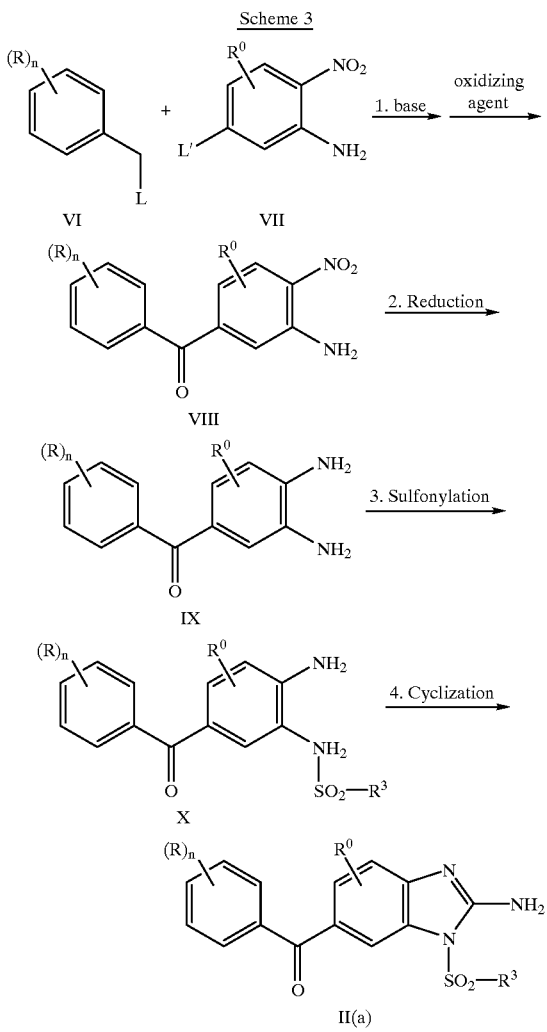

Reaction 3.1 may be accomplished by first exposing an appropriately substituted halo-nitroaniline of formula VII and an appropriately substituted phenylacetonitrile or benzoate of formula VI to a base in an organic solvent for one to twenty four hours at a temperature of from about −10° C. to about 40° C. to form a cyano or ester intermediate. The reaction is typically carried out using equimolar proportions of the reactants in the presence of two equivalents of the base. Typical bases include sodium hydride, potassium t-butoxide, and lithium diisopropylamide (LDA). A preferred base is potassium t-butoxide. Examples of solvents suitable for use in this reaction include dimethylformamide, dimethylacetamide, and the like. This intermediate is generally prepared in from about one to fifteen hours when the reaction is initiated at 0° C. and allowed to progress at room temperature. The cyano or ester intermediate is preferably oxidized in the same reaction mixture without prior isolation or purification.

In particular, the cyano or ester intermediate is reacted with an oxidizing agent for thirty minutes to fifteen hours at a temperature of from about 0° C. to about 30° C. to provide the compound of formula VIII. Typical oxidizing agents include hydrogen peroxide, oxygen, and air. The oxygen and air are typically bubbled through the reaction mixture. A preferred oxidizing agent is hydrogen peroxide, preferably in a 30% solution. The compound of formula VIII is generally prepared in from about five to thirty hours when the reaction is carried out between 0° C. and room temperature. The reaction is preferably monitored by TLC, for example, to ensure that the reaction goes to completion.

In reaction 3.2, the nitro substituent on the compound of formula VIII is reduced according to procedures known in the art to provide the corresponding diaminobenzophenone compound of formula IX. For example, the nitro substituent may be reduced by catalytic hydrogenation by combining the compound of formula VIII with hydrogen gas in ethanol or tetrahydrofuran and a catalyst. A preferred catalyst is palladium-on-carbon or Raney nickel. The hydrogen gas is typically used at a pressure of up to 60 psi, preferably at or about 30 psi. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 5 hours.

In reaction 3.3, the diaminobenzophenone compound of formula IX may be sulfonylated with an appropriately substituted sulfonyl halide of the formula $R^2$—$SO_2$-halo substantially in accordance with the procedure detailed above for the sulfonylation of compounds of formula I to provide the corresponding sulfonamido benzophenone compounds of formula X.

In reaction 3.4, the compound of formula X is cyclized via a nitrile intermediate by first exposing the compound of formula X to a base in an alcoholic solvent such as isopropanol followed by reaction with cyanogen bromide. Typically, the compound of formula X and the base are reacted at a temperature of from about 0° C. to about 30° C. A preferred base is sodium hydroxide, preferably added in the form of an aqueous solution (about 1–4M). When the compound of formula X is completely dissolved, the resultant solution is combined with cyanogen bromide. The cyanogen bromide is typically added in the form of a solution (3–7M for example in acetonitrile). The reaction is generally complete after one to eighteen hours when the reaction mixture is stirred at room temperature. However, in certain instances the nitrile intermediate will precipitate out of the reaction mixture. This precipitate is isolated and then refluxed in an alcoholic solvent such as isopropanol for one to four hours to provide the desired ketone compound of formula II(a).

Alternatively, the compound of formula X is cyclized via a nitrile intermediate by exposing the sulfonamido benzophenone compound to a base in a chlorinated solvent such as methylene chloride followed by reaction with cyanogen bromide. Typically, the compound of formula X and the base are reacted at a temperature of from about 0° C. to about the reflux temperature of the mixture. A preferred base is lithium methoxide. The sulfonamido benzophenone and the base typically form a slurry which is then combined with cyanogen bromide. The cyanogen bromide is typically added in the form of a solution (3–7M for example in methylene chloride). The reaction is generally complete after one to eighteen hours when the reaction mixture is stirred at a temperature range of 0° C. to the reflux temperature of the solvent. Compounds of formula II(a) may then be converted to the other compounds of formula II by the procedures discussed above for the acylation or sulfonylation of compounds of formula I.

The compounds of formula II where $R^2$ is not $SO_2R^3$ may be prepared substantially as described in Scheme 3 except that instead of using a compound of formula VII as a starting material in Scheme 3, Reaction 1 a compound of formula XI:

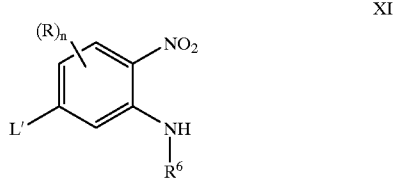

where $R^6$ is $C_1$–$C_6$ alkyl, $C_3$–$C_7$ cycloalkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, or a group of the formula:

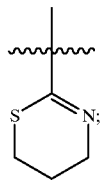

and L' is as defined above, is used instead.

The compounds of formula IV may be prepared from compounds of formula II as described in the previously incorporated U.S. Pat. No. 4,118,742 or as demonstrated in Example 15a–15b.

The compounds of formula XI are prepared by displacing the chloro or fluoro substituent on a compound of formula XII:

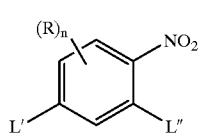

where L" is chloro or fluoro, with the proviso that L" cannot be chloro when L' is fluoro, with a primary amine of the formula $NH_2R^6$, where $R^6$ is as defined above, in an organic solvent. The reaction is optionally carried out in the presence of an acid scavenger such as potassium carbonate or a large excess of the primary amine. Typical solvents include tetrahydrofuran, dimethylformamide, dimethylacetamide and the like. The reaction is generally complete in one to twenty hours when carried out at a temperature of from about 2° C. to about 8° C. The resultant alkylated halo nitroaniline is then reacted as described in Scheme 3, above.

It will be understood by those in the art that in performing the processes described above it may be desirable to introduce chemical protecting groups into the reactants in order to prevent secondary reactions from taking place. Any amino, hydroxy, alkylamino, or carboxy groups which may be present on the reactants may be protected using any standard amino, hydroxy, or carboxy-protecting group which does not adversely effect the remainder of the molecule's ability to react in the manner desired. The various protective groups may then be removed simultaneously or successively using methods known in the art. It is within the knowledge of one skilled in the art to select appropriate amino, hydroxy, or carboxy protecting group(s) for a given set of reaction conditions given the guidance provided by Greene, Haslam, and Barton cited above.

In general, solvent choice in the transformations of Schemes 1–3 is not critical so long as the solvent employed is inert to the ongoing reaction and the reactants are sufficiently solubilized to effect the desired reaction. The optimal time for performing the reactions of the invention can be determined by monitoring the progress of the reaction via conventional chromatographic techniques such as TLC or HPLC analysis. Furthermore, conducting the reactions of the invention under an inert atmosphere, such as, for example, argon, or, particularly, nitrogen may be advantageous. Once a reaction is complete, the intermediate compound may be isolated, if desired, by procedures known in the art. For example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme. The compounds of formula II, IV, VIII, IX, X, and XI, and XII are preferably isolated and purified before their use in subsequent reactions.

The compounds employed as initial starting materials in the synthesis of the compounds of this invention are known in the art, and, to the extent not commercially available, are readily synthesized by standard procedures commonly employed in the art.

The following Examples further illustrate specific aspects of the present invention. It is to be understood, however, that these examples are included for illustrative purposes only and are not intended to limit the scope of the invention in any respect and should not be so construed.

EXAMPLES

In the following Examples, nuclear magnetic resonance spectra, field desorption mass spectra, infrared spectra, ultraviolet spectra, elemental analysis, high performance liquid chromatography, and thin layer chromatography are abbreviated "NMR", "MS(FD)", "IR", "UV", "Analysis", "HPLC", and "TLC", respectively. The MS(FD) data is presented as the mass number unless otherwise indicated. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "p" is pentet, "m" is multiplet, and "dm" is a doublet of multiplets. "J" indicates the coupling constant in Hertz (Hz). Unless otherwise noted, NMR data refers to the free base of the subject compound. The chemical shifts for NMR data are expressed in delta, δ values (parts per million downfield from tetramethyl-silane).

Example 1

A. 3-Amino-4-nitro-4'-fluorobenzophenone

To a cold (0° C.) solution of 17.25 g (100 mmol) of 5-chloro-2-nitroaniline and 12 ml (100 mmol) of 4-fluorophenylacetonitrile in 200 ml of dimethylformamide, was added 22.44 g (200 mmol) of potassium t-butoxide, under nitrogen. The resultant reaction mixture was warmed to room temperature and reacted overnight. When the reaction was substantially complete, as indicated by TLC (eluent of 40% ethyl acetate in hexane), the reaction mixture was cooled to 0° C. followed by the addition of 30 ml of hydrogen peroxide. When the reaction was substantially complete, as indicated by TLC (eluent of 40% ethyl acetate in hexane), the reaction mixture was poured into 1 liter of 1N hydrochloric acid (aqueous) which resulted in the formation of a yellow/orange precipitate. This precipitate was isolated by filtration.

Yield: 23.3 g (89%).

B. 3,4-Diamino-4'-fluorobenzophenone

To a solution of 21 g of the subtitled compound of Example 1A in 250 ml of tetrahydrofuran and 250 ml of ethanol, was added 3.0 g of Raney Nickel catalyst. The resultant reaction mixture was stirred overnight under 30 psi of hydrogen (gas) and then filtered. The resultant filtrate was concentrated in vacuo to provide a yellow solid which was used without further purification.

$^1$H NMR (DMSO-$d_6$) δ 7.65 (dd, J=7, 5 Hz, 2H), 7.30 (dd, J=7, 7 Hz, 2H), 7.04 (d, J=2 Hz, 1H), 6.90 (dd, J=7, 2 Hz, 1H), 6.53 (d, J=7 Hz, 1H), 5.49 (bs, 2H), 4.73 (bs, 2H). MS(FD) (MeOH) m/z 230.

C. 4-Amino-3-isopropylsulfonamido-4'-fluorobenzophenone

To a solution of 18.14 g (79 mmol) of the subtitled compound of Example 1B in 160 ml of anhydrous methylene chloride and 32 ml of anhydrous pyridine, was added 13.25 ml (118 mmol) of isopropylsulfonylchloride. The resultant reaction mixture was reacted at room temperature for approximately five hours, under nitrogen. When the reaction was substantially complete, as indicated by TLC (eluent of ethyl acetate), the reaction mixture was poured into 400 ml of 1N hydrochloric acid (aqueous). The resulting mixture was diluted with 300 ml of ethyl acetate and the resulting layers were separated, the organic layer dried over magnesium sulfate, filtered and concentrated in vacuo to provide a dark red gum. This gum was purified using Preparatory HPLC (gradient eluent of 30–60% ethyl acetate in hexane). The fractions containing the desired compound were combined and dried in vacuo to provide 17.11 g of a yellow gum that was used without further purification.

Yield: 65; $^1$H NMR (DMSO-$d_6$) δ 8.89 (s, 1H), 7.73 (dd, J=7, 5 Hz, 2H), 7.65 (d, J=2 Hz, 1H), 7.46 (dd, J=7, 2 Hz, 1H), 7.36 (dd, J=7, 7 Hz, 2H), 6.82 (d, J=7 Hz, 1H), 6.12 (bs, 2H), 3.24 (septet, J=6 Hz, 1H), 1.27 (d, J=6 Hz, 6H). MS(FD) m/z 336.

D. 1-Isopropylsulfonyl-2-Amino-6-(4-Fluorobenzoyl)benzimidazole

To a solution of 17.11 g (51 mmol) of the subtitled compound of Example 1C and 25 ml of 2N sodium hydroxide (aqueous) in 100 ml of isopropanol, was added 10 ml of a 5M cyanogen bromide. The resultant reaction mixture was reacted at room temperature for approximately thirty minutes resulting in the formation of a precipitate. This precipitate was isolated by filtration to provide 11.68 g of a solid. This solid was resuspended in 250 ml of isopropanol and the resultant mixture was refluxed until all of the material had dissolved and then cooled to provide 10.0 g of the desired compound. (55%).

EA calculated for $C_{17}H_{16}FN_3O_3S$: C, 56.50; H, 4.46; N, 11.63. Found: C, 56.71; H, 4.48; N, 11.82. MS(FD): 361.

The compounds in Examples 2–6 were prepared substantially in accordance with the procedure detailed in Example 1A–1D.

Example 2

1-Isopropylsulfonyl-2-Amino-6-(3-Fluorobenzoyl)benzimidazole

MS(FD): 361.2. $^1$H NMR (300 MHz; $d_6$-DMSO): δ 1.25 (d, 6H); 3.95 (m, 1H); 7.25–7.70 (m, 6H); 7.95 (s, 1H).

Example 3

1-Isopropylsulfonyl-2-Amino-6-(3-Fluoro-4-Methoxybenzoyl)benzimidazole

EA Calculated for $C_{18}H_{18}FN_3O_4S$: C, 55.23; H, 4.63; N, 10.73. Found: C, 55.12; H, 4.65; N, 10.53.

MS(FD): 391.2.

Example 4

1-Isopropylsulfonyl-2-Amino-6-(3,5-Difluorobenzoyl)benzimidazole

EA Calculated for $C_{17}H_{15}F_2N_3O_3S$: C, 53.82; H, 3.99; N, 11.08. Found: C, 53.63; H, 3.90; N, 11.03. MS(FD): 379.3. $^1$H NMR (300 MHz; $d_6$-DMSO): δ 1.30 (d, 6H); 3.95 (m, 1H); 7.31–7.65 (m, 7H); 7.95 (s, 1H).

Example 5

1-Isopropylsulfonyl-2-Amino-6-(3,4-Diflurobenzoyl)benzimidazole

EA Calculated for $C_{17}H_{15}F_2N_3O_3S$: C, 53.82; H, 3.99; N, 11.08. Found: C, 53.63; H, 4.05; N, 11.33. MS(FD): 379.1. $^1$H NMR (300 MHz; $d_6$-DMSO): δ 1.30 (d, J=2.4 Hz, 6H); 3.95 (septet, J=2.4 Hz, 1H); 7.35 (d, J=2.5 Hz, 1H); 7.46 (s, 2H); 7.56–7.80 (m, 3H); 7.75–7.85 (m, 1H); 7.94 (s, 1H).

Example 6

1-Isopropylsulfonyl-2-Amino-6-(2,3-Diflurobenzoyl)benzimidazole $^1$H NMR (300 MHz, DMSO-$d_6$) δ 7.90 (s, 1H) 7.20–7.80 (m, 5H), 3.90 (p, J=6.89 Hz, 1H), 1.30 (d, J=6.89 Hz, 6H).

Example 7

1-Isopropylsulfonyl-2-Amino-6-(1-[2,3-Difluorophenyl]-2-Carboxyethen-1-yl)benzimidazole t-Butyl acetate (1.67 ml, 12.3 mmol) and 4 ml of tetrahydrofuran were placed in a flask and cooled to −78° C. Lithium bis(trimethylsilyl)amide (12.3 ml, 12.3 mmol) was added slowly keeping the temperature below −70° C. The resulting solution was allowed to stir for 1 hour at −78° C. The 1-isopropylsulfonyl-2-amino-6-(2,3-difluorobenzoyl) benzimidazole (1.17 g, 3.07 mmol) in 12 ml of tetrahydrofuran was then added slowly keeping the temperature below −60° C. The reaction was monitored at −78° C. by HPLC (65% methanol:buffer 0.5% triethylamine,0.3% phosphoric acid) and when the ketone was consumed (about 30 minutes), 2 ml of concentrated hydrochloric acid was added, and the mixture was allowed to warm to room temperature. The reaction was concentrated in vacuo and the residue was taken up in 35 ml of 96% formic acid and 0.5 ml of concentrated hydrochloric acid. The resulting mixture was heated to 95° C. After 4 hours, the reaction was concentrated in vacuo and diluted to 11 ml with acetonitrile. The crude product was purified by reverse phase chromatography (35% acetonitrile:water) to give 152 mg of cis product and 163 mg of trans product. (27.0%).

Data for cis: $^1$H NMR (300 MHz, DMSO-d$_6$) δ 12.48 (s, 1H) 7.60–7.35 (m, 2H), 7.35–7.00 (m, 5H), 6.98 (dd, J=8.94, 3.4 Hz, 1H), 6.20 (s, 1H), 3.82 (p, J=6.88 Hz, 1H), 1.21 (d, J=6.88 Hz, 6H). UV/Vis (95% EtOH) $\lambda_{max}$, (ε): 318 (18786), 246 (15054).

Data for trans: MS(FD) m/z 420.9. EA Calculated for $C_{19}H_{17}F_2N_3O_4S$: C, 54.14; H, 4.07; N, 9.97. Found: C, 53.99; H, 3.98; N, 9.99.

Example 8

Trans 1-Isopropylsulfonyl-2-Amino-6-(1-[2,3-Difluorophenyl]-2-Methylsulfonylethen-1-yl) benzimidazole Methyl sulfone (1.23 g, 13.2 mmol) was dissolved in 6 ml of tetrahydrofuran and cooled to −78° C. n-Butyl lithium (5.30 ml, 13.3 mmol) was then added slowly keeping the temperature below −68° C. The resulting solution was allowed to stir at −78° C. for 2 hours. The 1-isopropylsulfonyl-2-amino-6-(2,3-diflurobenzoyl) benzimidazole (832 mg, 2.20 mmol) was then added in 6 ml of tetrahydrofuran and the mixture was allowed to warm to room temperature slowly overnight. The reaction was transferred to a separatory funnel and partitioned between 150 ml of 1N hydrochloric acid and 250 ml of hydrochloric acid. The aqueous layer was extracted with chloroform and then again with 250 ml of ethyl acetate. The organic extracts were combined and washed with 100 ml of brine, dried over magnesium sulfate, filtered, and concentrated in vacuo. The residue was taken up in 0.5 ml of concentrated hydrochloric acid and 35 ml of 96% formic acid and the resulting solution was heated to 95° C. for 2 hours. The reaction was cooled to room temperature and concentrated in vacuo. The residue was diluted to 11 ml with acetonitrile and the crude mixture was purified by reverse phase chromatography in a step gradient (6 L 32% acetonitrile:water, 2 L each of 33, 34, 35, 36, 37% acetonitrile:water) to give 60 mg of pure trans product. (5.7%).

MS(FD) m/z 455. EA calculated for $C_{19}H_{19}F_2N_3O_4S_2$ C, 50.10; H, 4.20; N, 9.23. Found: C, 49.88; H, 4.28; N, 9.16.

Example 9

1-Isopropylsulfonyl-2-Amino-6-(1-[2,3-Difluorophenyl]-2-Methylsulfidoethen-1-yl) benzimidazole TMEDA was added slowly to a solution of n-butyl lithium (7.88 mL, 2.5M in hexane) at room temperature. The temperature was maintained during the addition by cooling with a water bath. Dimethylsulfide (1.45 mL, 19.7 mmol) was added slowly and the resulting mixture was allowed to stir for 4.5 hours. The reaction was cooled to −40° C. and 1-isopropylsulfonyl-2-amino-6-(2,3-diflurobenzoyl) benzimidazole (1.49 g, 3.94 mmol) dissolved in 35 mL of tetrahydrofuran at −40° C. was added slowly via a cannula. After the addition was complete, the mixture was allowed to warm to room temperature slowly overnight. The reaction was partitioned between 250 mL of chloroform and 250 mL of 1N hydrochloric acid. The organics were washed with 250 mL of iN hydrochloric acid, 250 mL of brine, dried over magnesium sulfate, filtered, and concentrated in vacuo. The residue was taken up in 12 mL of 96% formic acid and heated to 95° C. for 4 hours. The solvents were removed in vacuo, the residue taken up in 11 mL of 50:50 acetonitrile water, and the crude product solution was purified via reverse phase HPLC (46% acetonitrile:water) to give 100 mg of trans product and 100 mg of cis product.

Data for trans: MS(FD) 423.

Data for cis: MS(FD) 423.

Example 10

Trans 1-Isopropylsulfonyl-2-Amino-6-(1-[2,3-Difluorophenyl]-2-(Methylsulfinylethen-1-yl) benzimidazole The trans 1-isopropylsulfonyl-2-amino-6-(1-[2,3-difluorophenyl]-2-methylsulfidoethen-1-yl)benzimidazole (81.9 mg, 0.194 mmol) was dissolved in 3 mL of methanol and oxone (475 mg, 1.54 mmol equivalents) dissolved in 3 ml of water was added. The resulting mixture was allowed to stir for 5 hours and then 200 mL of ethyl acetate were added along with 50 mL of saturated aqueous sodium bicarbonate. The contents were partitioned and the aqueous layer was removed. The organics were washed with brine, dried over magnesium sulfate, filtered, and concentrated in vacuo. The crude material was dissolved in dimethylsulfoxide and purified via reverse phase HPLC (45% acetonitrile:water) to give 15.9 mg of the title compound. (18.0%)

MS(FD) 439.

Example 11

Trans 1-Isopropylsulfonyl-2-Amino-6-(1-[2,3-Difluorophenyl]-2-(1-Oxoeth-1-yl)ethen-1-yl) benzimidazole In an oven dried 3-neck flask fitted with a septum, condenser, and addition funnel was placed magnesium (503 mg, 20.7 mmol), mercury II chloride (48.3 mg, 0.178 mmol), and 73 mL of anhydrous ether. Propargyl bromide (1.96 mL, 17.6 mmol) was added slowly via the addition funnel. After addition was complete the mixture was sonicated for 30 minutes to form the Grignard reagent.

In a separate flask was placed the 1-isopropylsulfonyl-2-amino-6-(2,3-diflurobenzoyl)benzimidazole (1.94 g, 5.13 mmol) and 30 mL of anhydrous ether. Sodium hydride (205 mg, 5.13 mmol) was added and after the foaming had ceased the Grignard reagent was added in 14 mL portions for a total of 62 mL. The reaction was partitioned between 250 mL of ethyl acetate and 250 1N hydrochloric acid. The organics were separated and washed with 150 mL of brine then dried over magnesium sulfate. The solution was concentrated in vacuo, then dissolved in 50 mL of methylene chloride. 25 mL of the crude product solution were removed to be used in Example 11, and the remaining solution was concentrated in vacuo then redissolved in 10 mL of glacial acetic acid and 1 mL of sulfuric acid. The solution was heated to 75° C. for 1 hour. The reaction was cooled to room temperature and 50 mL of water were added. The mixture was extracted with methylene chloride (3×125 mL) and the organics were combined and washed with 50 mL of water, 50 mL of saturated sodium bicarbonate, dried over sodium sulfate, filtered, and concentrated in vacuo. The residue was diluted to 11 mL with acetonitrile and the crude material was purified by reverse phase chromatography (42% acetonitrile:water) to give 166 mg of trans product. (23.1%).

MS(FD) m/z 419.0. EA calc'd for $C_{20}H_{19}F_2N_3O_3S$ C, 57.27; H, 4.57; N, 10.02. Found: C, 57.20; H, 4.56; N, 10.28.

Example 12

Trans 1-Isopropylsulfonyl-2-Amino-6-(1-[2,3-Difluorophenyl]-2-(Carboxymethylethen-1-yl) benzimidazole A three neck flask fitted with a septum, stir bar, condenser, stopper, and a thermocouple was purged twice with $N_2$ and charged with 8 mL of dry tetrahydrofuran and methyl (trimethylsilyl)acetate (1.736 mL, 10.58 mmol). The solution was cooled to −78° C. and lithium bis(trimethylsilyl) amide (10.34 mL, 10.34 mmol) was added slowly keeping the temperature below −50° C. After the addition was complete, the solution was cooled to −78° C. and stirred for 30 minutes. The 1-isopropylsulfonyl-2-amino-6-(2,3-diflurobenzoyl)benzimidazole (980 mg, 2.58 mmol) in 10 mL of dry tetrahydrofuran was then added via cannula and the resulting mixture was allowed to stir at −78° C. for 2 hours. The mixture was allowed to warm slowly to 5° C., and then was heated to 55° C. for 2 hours. The progress of the reaction was monitored by HPLC (65% methanol:buffer 0.5% triethylamine, 0.3% phosphoric acid). The reaction was allowed to cool to room temperature and was quenched with 25 mL of saturated ammonium chloride. The tetrahydrofuran was removed in vacuo and the residue was taken up in 300 mL of ethyl acetate. The organics were washed with 1N hydrochloric acid (2×100 mL), brine (1×100 mL), dried over sodium sulfate, filtered, and concentrated in vacuo. The residue was diluted to 11 mL with acetonitrile and the crude reaction mixture was purified by reverse phase chromatography (44% acetonitrile:water) to give 230 mg of trans product. (20.5%).

MS(FD) (MeOH) m/z 435. EA calculated for $C_{20}H_{19}F_2N_3O_4S$: C, 55.17; H, 4.40; N, 9.65. Found: C, 55.36; H, 4.61; N, 9.52.

Example 13

Trans 1-Isopropylsulfonyl-2-Amino-6-(1-[2,3-Difluorophenyl]oximyl)benzimidazole

The 1-isopropylsulfonyl-2-amino-6-(2,3-diflurobenzoyl) benzimidazole (1.08 g, 2.86 mmol), 13 ml of methanol, hydroxylamine hydrochloride (993 mg, 14.3 mmol), and 5.2 ml of pyridine were combined in a round bottom flask. The suspension was allowed to stir for 6 days monitoring for disappearance of the ketone starting material by HPLC (65% methanol:buffer, 0.5% triethylamine, 0.3% phosphoric acid). Only one isomer formed. By the time the reaction was complete the contents of the reaction were all in solution. The reaction was transferred to a separatory funnel and 600 ml of ethyl acetate were added. The organics were washed with 1N hydrochloric acid (4×100 ml) and brine (1×100 ml). The aqueous washes were back extracted with 600 ml of ethyl acetate. The combined organics were dried over magnesium sulfate, filtered, and concentrated in vacuo. The residue was diluted to 11 ml with acetonitrile and purified by reverse phase chromatography (34% acetonitrile:water) to give 133 mg of trans product. (11.8%).

$^1$H NMR (300 MHz, DMSO-d$_6$) δ 11.55 (s, 1H) 7.78 (d, 1H, J=1.2), 7.49 (q, 1H, J=8.6), 7.28 (q, 1H, J=6.3), 7.15 (d, 1H, J=8.6), 7.09 (s, 2H), 7.02–7.07 (m, 1H), 7.00 (dd, 1H, J=8.6, 1.2), 3.80 (p, 1H, J=6.99), 1.49 (d, 6H, J=6.99). IR (KBr) υ 3449, 3164, 1649, 1611, 1590, 1559 cm$^{-1}$. MS(MS) (MeOH) m/z 394.1. EA calc'd for $C_{17}H_{16}F_2N_4O_3S$: C, 51.77; H, 4.09; N,14.21. Found: C, 51.96; H, 4.24; N, 13.92.

Example 14

1-Isopropylsulfonyl-2-Amino-6-(1-[4-Fluorophenyl]-2-(1-Oxoeth-1-yl)ethen-1-yl) benzimidazole In an oven dried 3-neck flask fitted with a septum, condenser, and addition funnel was placed magnesium, mercury II chloride, and anhydrous ether. Propargyl bromide was added slowly via the addition funnel. After the addition was complete the mixture was sonicated for 30 minutes to form the Grignard reagent.

In a separate flask was placed the 1-isopropylsulfonyl-2-amino-6-(2,3-diflurobenzoyl)benzimidazole and anhydrous ether. Sodium hydride was added and after the foaming had ceased the Grignard reagent was added. The reaction was partitioned between ethyl acetate and 1N hydrochloric acid. The organics were separated and washed with brine then dried over magnesium sulfate. The solution was concentrated in vacuo to give 12.0 g of the intermediate carbinol.

The intermediate was dissolved in 500 mL of methylene chloride. Dimethylaminopyridine (9.0 g) and triethylamine (18.7 mL) were then added and the reaction was cooled to −78° C. Methanesulfonylchloride (8.8 mL) was added and the reaction was allowed to warm slowly to room temperature overnight. The reaction was concentrated to remove the methylene chloride and the residue was dissolved in 500 mL of ethyl acetate. 100 mL of 1N hydrochloric acid was added and the resulting mixture was allowed to stir for 1 hour. The mixture was then partitioned and the aqueous layer was removed and back extracted with ethyl acetate. The organics were washed with 1N hydrochloric acid (2×100 mL), dried over magnesium sulfate, filtered, and concentrated in vacuo. The intermediates were partially converted to product by treatment with trifluoroacetic acid and the crude mixture was purified via reverse phase HPLC (60:40 acetonitrile:water) to give 500 mg of trans and 500 mg of cis.

Data for trans: MS(FD) 401. IR (CHCl$_3$) υ 3397, 1640, 1603 cm$^{-1}$.

Data for cis: EA calc'd for $C_{20}H_{20}N_3O_3S$: C, 59.84; H, 5.02; N, 10.47. Found: C, 60.20; H, 5.06; N, 10.46. MS(FD) 401.

Example 15

Trans-1-Isopropylsulfonyl-2-Amino-6-(1-[2,5-Difluorophenyl]-2-(Bromo)ethen-1-yl)benzimidazole
A. 2-Amino-α-(2,5-Difluorophenyl)-α-Methyl-1-[(1-methylethyl)sulfonyl]benzimidazole-6-Methanol Methyl magnesium chloride (929 mL, 2.79 mol, 3M in tetrahydrofuran) was added slowly over 30 minutes to a solution of 1-isopropylsulfonyl-2-amino-6-(2,5-difluorobenzoyl)benzimidazole (352.7 g, 0.929 mol) in tetrahydrofuran while maintaining the temperature between −20° C. and −30° C. When the addition was complete, the reaction mixture was warmed slowly to room temperature over 2 hours. Additional 3M methyl magnesium chloride (186 mL, followed by 46.5 mL) was added until less than 1% ketone starting material remained by HPLC analysis. The reaction was quenched by the sequential addition of ethyl acetate (4.2 L) and 1N hydrochloric acid (4.2 L) and the mixture stirred for 1 hour. The phases were separated and the aqueous phase extracted with ethyl acetate (2.0 L). The combined organic fractions were washed with brine (4.0 L) and dried over magnesium sulfate. After filtration, removal of the solvent by rotary evaporation afforded 373 g of the title compound as a beige foam (93% purity, 94% yield).

¹H NMR (CDCl₃) δ 1.34 (m, 6H), 1.99 (s, 3H), 3.02 (br s, 1H, D₂O exch), 3.56 (septet, J=6.9 Hz, 1H), 6.02 (br s, 2H, D₂O exch), 6.88–6.93 (m, 2H), 7.18 (dd, J=8.3, 1.7 Hz, 1H), 7.22 (d, J=8.4 Hz, 1H), 7.40–7.43 (m, 1H), 7.71 (d, J=1.2 Hz, 1H). EA Calculated for C₁₈H₁₉F₂N₃O₃S: C, 54.68; H, 4.84; N, 10.63; S, 8.11. Found: C, 54.94; H, 4.84; N, 10.35; S, 8.10.

B. 1-Isopropylsulfonyl-2-Amino-6-(1-[2,5-Difluorophenyl]ethen-1-yl)benzimidazole Methanesulfonic acid (33.0 g, 344 mmol) was added to a solution of 2-amino-α-(2,5-difluorophenyl)-α-methyl-1-[(1-methylethyl)sulfonyl]benzimidazole-6-methanol (53.4 g, 97% purity, 115 mmol) in methylene chloride (500 mL) and the solution turned from beige to brown. The solution was heated at reflux for 1.5 hours until the reaction was complete. After cooling to room temperature, a saturated aqueous solution of sodium bicarbonate (200 mL) was added to neutralize the acid. However, the pH remained at 1 and extensive foaming occurred. The reaction mixture was then neutralized to pH 7–8 with 1N sodium hydroxide (about 90 mL) while keeping the temperature at 20° C. The phases were separated and the organic phase extracted with methylene chloride (100 mL). The combined organic fractions were washed with brine (100 mL) and dried over sodium sulfate. The hazy mixture was filtered to give a clear burnt-orange solution which was concentrated by rotary evaporation at 40–70° C. to give 39.9 g of the title compound as a beige powder (98.5% purity, 91% yield), mp 161.0–164.5° C.

¹H NMR (CDCl₃) δ 1.39 (d, J=6.8 Hz, 6H), 3.63 (septet, J=6.9 Hz, 1H), 5.43 (s, 1H), 5.75 (s, 1H), 6.16 (s, 2H), 6.98–7.04 (m, 3H), 7.16 (dd, J=8.2, 1.7 Hz, 1H), 7.28 (d, J=8.3 Hz, 1H), 7.59 (d, J=1.6 Hz, 1H). EA Calculated for C₁₈H₁₇F₂N₃O₂S: C, 57.26; H, 4.54; N, 11.13; F, 10.07; S, 8.50. Found: C, 57.50; H, 4.54; N, 11.06; F, 10.12; S, 8.21.

C. Trans-1-Isopropylsulfonyl-2-Amino-6-(1-[2,5-Difluorophenyl]-2-(Bromo)ethen-1-yl)benzimidazole 1-Isopropylsulfonyl-2-amino-6-(1-[2,5-difluorophenyl]ethen-1-yl)benzimidazole (39.46 g, 103.0 mmol) was dissolved in tetrahydrofuran (197 mL) and the resulting solution diluted with carbon tetrachloride (197 mL) and cooled to 0° C. A 1M solution of Br₂ (18.4 g, 115 mmol) in carbon tetrachloride was added over 30 min. A beige slurry formed at the mid-point of the addition and became yellow by the end of the addition. The addition/elimination reaction is complete soon after the bromine has been added, but to equilibrate the E/Z-vinyl bromides, the reaction was stirred for an additional 2.5 hours at room temperature. After cooling the mixture to 0° C., 10% Na₂S₂O₃ (50 mL) and 1N aqueous sodium hydroxide (ca. 105 mL) were added and the pH adjusted to 5–6. Methylene chloride (200 mL) was added to dissolve particulate material in the lower organic phase and the phases were separated. The aqueous phase was extracted with methylene chloride (50 mL) and the combined organic fractions were washed with water (200 mL) and brine (200 mL) and then dried over sodium sulfate. Filtration, followed by removal of the solvent by rotary evaporation afforded 48.88 g of a beige solid containing a 95:5 mixture of Z- and E-vinyl bromides and 2.8% tetrahydrofuran by weight (¹H NMR). Recrystallization from acetonitrile (250 mL) afforded 33.8 g of the title compound (97.8% purity, 99+% Z-isomer by ¹H NMR, 71% yield) as a pale yellow powder, mp 180.5–181.9 (dec). An additional 2.17 g (92.5% purity, 4.5% yield) was obtained in a second crop from acetonitrile.

¹H NMR (CDCl₃) δ 1.39 (d, J=6.9 Hz, 6H), 3.62 (septet, J=6.8 Hz, 1H), 6.52 (s, 2H), 6.92 (s, 1H), 6.97–7.00 (m, 1H), 7.02 (dd, J=8.3, 1.8 Hz, 1H), 7.08–7.12 (m, 2H), 7.23 (d, J=8.3 Hz, 1H), 7.54 (s, 1H). EA Calculated for C₁₈H₁₆BrF₂N₃O₂S: C, 47.36; H, 3.53; N, 9.21; Br, 17.51; S, 7.03. Found: C, 47.66; H, 3.44; N, 9.32; Br, 17.59; S, 6.97.

Example 16

Trans-1-Isopropylsulfonyl-2-Amino-6-(1-[3-Fluorophenyl]-2-(Iodo)ethen-1-yl)benzimidazole Phenyllithium (5.7 mL, 1.8M in 70:30 cyclohexane:ether, 10.3 mmol) was added to a tetrahydrofuran solution of trans-1-isopropylsulfonyl-2-amino-6-(1-[3-fluorophenyl]-2-(bromo)ethen-1-yl)benzimidazole (2.25 g, 5.13 mmol) over 15 minutes at −75° C. When the addition was complete, tert-butyllithium (6.18 mL, 1.7M in pentane, 10.5 mmol) was added over 20 minutes and the resulting slurry stirred for 10 minutes. A solution of 1,2-chloroiodoethane (1.03 g, 5.38 mmol) in tetrahydrofuran (3 mL) was added over 20 minutes at −80° C. During the addition the red-black mixture became emerald-green in color. The solution was stirred for 45 minutes, during which time it became a yellow-orange solution. The reaction was quenched by the addition of methanol (1 mL) at −7° C. and the addition of Na₂S₂O₃ (50 mL) at −35° C. The mixture was added to ethyl acetate (150 mL) and the phases-separated. The organic phase was washed with a brine (50 mL) and was dried over magnesium sulfate. After filtration, the solvent was removed by rotary evaporation giving 2.43 g of vinyl iodide which was an 80:20 mixture of Z- and E-isomers, respectively. Recrystallization from isopropanol (15 mL/g) afforded the title compound in 31% overall yield and 96% purity as a 97:3 mixture of Z- and E-isomers, respectively.

¹H NMR (DMSO-d₆) δ 1.23 (d, J=6.8 Hz, 6H), 3.90 (septet, J=6.8 Hz, 1H), 7.02–7.07 (m, 5H), 7.15 (d, J=8.3 Hz, 1H), 7.24–7.28 (m, 2H), 7.35 (d, J=1.1 Hz, 1H), 7.51 (q, J=6.4 Hz, 1H).

The term "effective amount" as used herein, means an amount of a compound of formula I which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium); ointments containing, for example, up to 10% by weight of the active compound, soft and hard gelatin capsules, suppositories, sterile injectable solutions, sterile packaged powders and the like.

The following formulation example is illustrative only and is not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

As noted above, the compounds of the present invention are useful as antiviral agents. They have shown inhibitory activity against various enteroviruses and rhinoviruses. An embodiment of the present invention is a method of inhibiting a picornavirus comprising administering to a host in need thereof an effective amount of a compound of formula I, or a pharmaceutically acceptable salt thereof.

The present compounds appear to inhibit replication of plus-strand viral RNA by interfering with the structure and/or function of the viral replication complex (a membrane-bound complex of viral and cellular proteins). Mutant rhinovirus and enterovirus have been isolated which demonstrate very low levels of drug tolerance. These mutants contain a single amino acid substitution in the protein that is expressed by the viral gene known as "3A". Therefore, the compounds of the present invention inhibit the rhinovirus and enterovirus by inhibiting a 3A function. The 3A gene encodes a hydrophobic protein which serves as the scaffolding protein that attaches the proteins of the replication complex to intracellular membranes.

The replicative strategy of flaviviruses such as hepatitis C virus (HCV) and bovine diarrheal virus (BVDV) is similar to that of the rhinovirus and enterovirus, discussed above. In particular, both families of virus contain single-stranded, messenger-sense RNA that replicates in a cytoplasmic complex via a minus-strand RNA intermediate. In addition, both families of virus translate their genome into a polyprotein that is subsequently cleaved. Furthermore, the replication complexes of both viruses are tightly associated with intracellular membranes. Finally, both families of virus have analogous genomic structures including the presence of a 5' and 3' non-translated region which are required by the viruses for replication. There are two HCV proteins that have been implicated with this intracellular association: NS2 and NS4. It is postulated that either NS2 or NS4 is analogous to the picornavirus 3A protein.

Accordingly, another embodiment of the present invention is a method for inhibiting a flavivirus comprising administering to a host in need thereof an effective amount of a compound of formula I, or a pharmaceutically acceptable salt thereof. It is preferred to inhibit hepatitis C.

Test Method for Anti-picornaviral Assay

African green monkey kidney cells (BSC-1) or Hela cells (5-3) were grown in 25 cc Falcon flasks at 37° C. in medium 199 with 5 percent inactivated fetal bovine serum (FBS); penicillin (150 units/ml) and streptomycin (150 micrograms per milliliter ($\mu$g/ml)). When confluent monolayers were formed, the supernatant growth medium was removed and 0.3 ml of an appropriate dilution of virus (rhinovirus, HRV-14) were added to each flask. After absorption for one hour at room temperature, the virus infected cell sheet was overlaid with a medium comprising one part of 1 percent Ionagar No. 2 and one part double strength Medium 199 with FBS, penicillin and streptomycin which contains drug at concentrations of 100, 50, 25, 12, 6, 3 and 0 $\mu$g/ml. The flask containing no drug served as the control for the test. The stock solutions of benzimidazole compounds were diluted with dimethylsulfoxide to a concentration of $10^4$ $\mu$g/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent can be used as a measure of activity. The 50 percent inhibition is indicated by the symbol $IC_{50}$.

Test results for various benzimidazole compounds are summarized in Table 1 by Example number and indicating the test virus and the percent inhibition of plaque reduction which is presented as an $IC_{50}$ value. Such $IC_{50}$ values represent the amount of test compound ($\mu$g/ml) that is needed to inhibit 50% of the plaque formation. All compounds in Table 1 were the trans isomer.

TABLE 1

| $IC_{50}$ ($\mu$g/mL) | |
|---|---|
| Example No | HRV-14 |
| 8 | 0.050 |
| 9 | 0.072 |
| 9 (parent) | 2.58 |
| 10 | 0.394 |
| 10 (parent) | 3.52 |
| 11 | 0.048 |
| 12 | 0.052 |
| 12 (parent) | 0.050 |
| 13 | 0.051 |
| 13 (parent) | 0.050 |
| 14 | 0.210 |

The notation "parent" in Table 1 refers to the compound with an identical substitution pattern to the example above it, except that the parent molecule is a compound where n is 0.

In vitro CPE/XTT anti-BVDV Assay

MDBK cells were dispersed in the 96-wells microtiter plate at 10,000 cells per well with Minimum Essential Medium containing Earl's balanced salt solution (EBSS), 2% horse serum, penicillin (100 units/ml) and streptomycin (100 μg/ml). Plates were grown at 37° C. $CO_2$ incubator overnight. The MDBK cells were then infected with 0.02 moi (multiplicity of infection) of bovine viral diarrhea virus (BVDV, ATCC VR-534). After allowing the virus to adsorb to the cells for 1–2 hours, medium containing serial dilutions of drug or medium alone was added to the wells. After further incubating for 3–4 days (when extensive cpe was apparent in medium alone wells), the antiviral effect of testing drugs were assessed by performing a XTT assay as described below.

XTT [2,3-bis(methoxy-4-nitro-5-sulfophenyl)-2H-tetraazolium-5-carboxanilide, inner salt, sodium salt] at 1 mg/ml for warm medium without FBS were freshly prepared and used immediately. For each 5 ml of the XTT solution, 25 μl of 5 mM of PMS (phenazine methosulfate) in phosphate buffer Table 1 saline was added. Then 50 μl of the freshly prepared XTT/PMS mixture was added to each of the microtiter wells. Incubate at 37° C. ($CO_2$) for 3–4 hours or until color change is prominent. Read absorbance at 450 nm/ref. 650 nm in a spectrophotometer. The concentration of drug required to cause 50% cytotoxic effect as compared to the no drug no virus control ($TC_{50}$) and which to inhibit the development of virus cytopathic effect (cpe) by 50% ($IC_{50}$) was then determined from the liner portion of each dose response curve.

We claim:

1. A compound of formula I

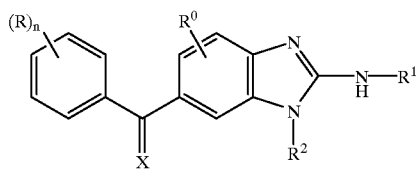

I wherein n is 2, 3, 4 or 5;

R is independently at each occurrence hydroxy, thiol, halo, cyano, cyano($C_1$–$C_4$)alkyl, amino, halo($C_1$–$C_4$) alkyl, ($C_1$–$C_4$)alkylamino, di($C_1$–$C_4$)alkylamino, azido, carboxy, $C_1$–$C_6$ alkyl, $C_2$–$C_6$ alkenyl, carbamoyl, carbamoyloxy, carbamoylamino, N-($C_1$–$C_4$)alkylcarbamoyl, —$OCF_3$, $OCCl_3$, $C_1$–$C_4$ alkoxy, $C_1$–$C_4$ alkoxycarbonyl, $C_1$–$C_4$ alkoxycarbonylamino, formyl, $C_2$–$C_4$ alkanoyl, formyloxy, $C_2$–$C_4$ alkanoyloxy, formylamino, $C_2$–$C_4$ alkanoylamino, $C_1$–$C_4$ alkylthio, $C_1$–$C_4$ alkylsulfinyl, $C_1$–$C_4$ alkylsulfonyl, pyrrolidino, piperidino or morpholino;

$R^0$ is hydrogen, halo, $C_1$–$C_4$ alkyl, or $C_1$–$C_4$ alkoxy;

$R^1$ is hydrogen, C(O)($C_1$–$C_6$ alkyl), $SO_2$($C_1$–$C_6$ alkyl), or C(O)$CF_3$;

$R^2$ is $C_1$–$C_6$ alkyl, $C_3$–$C_7$ cycloalkyl, halo($C_1$–$C_6$)alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, a group of the formula

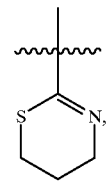

$SO_2R^3$, where $R^3$ is $C_1$–$C_{10}$ alkyl, halo($C_1$–$C_6$)alkyl, $C_3$–$C_7$ cycloalkyl, substituted $C_3$–$C_7$ cycloalkyl, phenyl, substituted phenyl, naphthyl, thienyl, thiazolidinyl, furyl, pyrrolidino, piperidino, morpholino, or $NR^4R^5_1$ where $R^4$ and $R^5$ are independently $C_1$–$C_4$ alkyl or $R^4$ and $R^5$ taken together with the nitrogen atom to which they are attached form a pyrrolidino, piperidino or morpholino ring; and X is NOZ or CHY, where Y is COZ, $CO_2Z$, or $S(O)_mZ$, where m is 0, 1, or 2 and Z is hydrogen or $C_1$–$C_{10}$ alkyl;

or a pharmaceutically acceptable salt thereof.

2. The compound of claim 1 wherein Y is $S(O)_mZ$, COZ, or $CO_2Z$.

3. The compound of claim 1 wherein

R is independently at each occurrence halo, $C_1$–$C_4$ alkyl, $C_1$–$C_4$ alkoxy or di($C_1$–$C_4$)alkylamino;

$R^0$ is hydrogen;

$R^1$ is hydrogen; and $R^2$ is $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino, morpholino or $SO_2R^3$, where $R^3$ is dimethylamino, $C_1$–$C_6$ alkyl, halo($C_1$–$C_6$)alkyl, $C_3$–$C_7$ cycloalkyl, or substituted $C_3$–$C_7$ cycloalkyl;

or a pharmaceutically acceptable salt thereof.

4. The compound of claim 3 wherein n is 2 or 3;

R is independently at each occurrence fluoro, methyl, ethyl, methoxy, ethoxy, or dimethylamino;

$R^2$ is $C_1$–$C_4$ alkyl, $C_3$–$C_7$ cycloalkyl, pyrrolidino, or $SO_2R^3$, where $R^3$ is dimethylamino, $C_1$–$C_4$ alkyl, or $C_3$–$C_7$ cycloalkyl; and Z is hydrogen or $C_1$–$C_4$ alkyl;

or a pharmaceutically acceptable salt thereof.

5. The compound of claim 4 wherein

R at each occurrence is fluoro;

$R^2$ is $C_1$–$C_4$ alkyl, $C_3$–$C_7$ cycloalkyl, or $SO_2R^3$, where $R^3$ is dimethylamino or $C_1$–$C_4$ alkyl; and Z is hydrogen or methyl;

or a pharmaceutically acceptable salt thereof.

6. A compound represented by structure I(b)

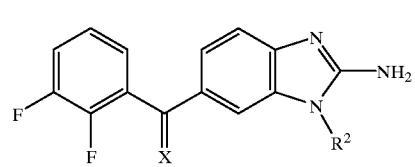

I(b)

wherein $R^2$ is $C_1$–$C_4$ alkyl, $C_3$–$C_7$ cycloalkyl, or $SO_2R^3$, where $R^3$ is dimethylamino or $C_1$–$C_4$ alkyl; and X is NOZ or CHY, where Y is $S(O)_mZ$, COZ, $CO_2Z$, or halo and Z is hydrogen or methyl;

or a pharmaceutically acceptable salt thereof.

7. The compound of claim 6 wherein said compound is represented by

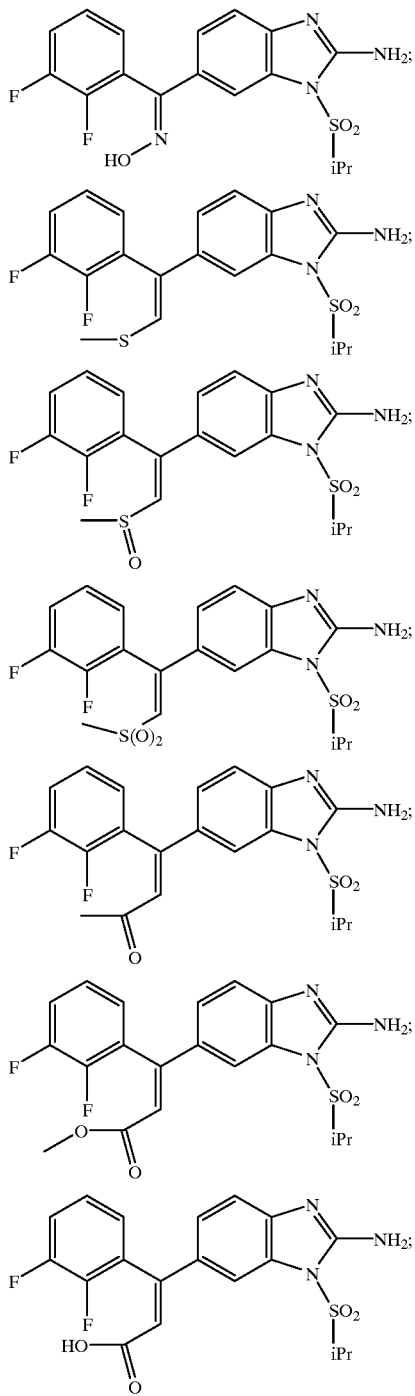

or a pharmaceutically acceptable salt thereof.

8. A pharmaceutical formulation comprising a compound of claim 1 associated with one or more pharmaceutically acceptable carriers, diluents, or excipients.

9. A method for inhibiting a hepatitis C virus or a bovine diarrheal virus comprising administering to a host in need thereof an effective amount of a compound of claim 1, wherein said compound of claim 1 inhibits the replication of said hepatitis C virus or said bovine diarrheal virus.

10. The method of claim 9 wherein said flavivirus is hepatitis C.

11. A method for inhibiting a rhinovirus or an enterovirus comprising administering to a host in need thereof an effective amount of a compound of claim 1, wherein said compound of claim 1 inhibits the 3A function of said rhinovirus or said enterovirus replication complex.

12. A process for preparing a compound of formula I(d):

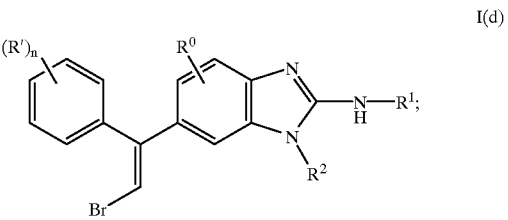

wherein:

n is 0, 1, 2, 3, 4 or 5;

R' is independently at each occurrence halo, cyano, cyano $(C_1-C_4)$alkyl, amino, halo$(C_1-C_4)$alkyl, $(C_1-C_4)$ alkylamino, di$(C_1-C_4)$alkylamino, azido, carboxy, $C_1-C_6$ alkyl, carbamoyl, carbamoyloxy, carbamoylamino, N-$(C_1-C_4)$alkylcarbamoyl, —OCF$_3$, OCCl$_{13}$, $C_1-C_4$ alkoxy, $C_1-C_4$ alkoxycarbonyl, $C_1-C_4$ alkoxycarbonylamino, formyl, $C_2-C_4$ alkanoyl, formyloxy, $C_2-C_4$ alkanoyloxy, formylamino, $C_2-C_4$ alkanoylamino, $C_1-C_4$ alkylthio, $C_1-C_4$ alkylsulfinyl, $C_1-C_4$ alkylsulfonyl, pyrrolidino, piperidino or morpholino;

$R^0$ is hydrogen, halo, $C_1-C_4$ alkyl, or $C_1-C_4$ alkoxy;

$R^1$ is hydrogen, C(O) ($C_1-C_6$ alkyl), SO$_2$ ($C_1-C_6$ alkyl); or C(O)CF$_3$; and $R^2$ is $C_1-C_6$ alkyl, $C_3-C_7$ cycloalkyl, halo$(C_1-C_6)$alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, a group of the formula

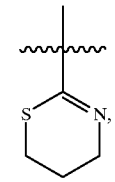

or SO$_2$R$^3$, where R$^3$ is $C_1-C_{10}$ alkyl, halo$(C_1-C_6)$alkyl, $C_3-C_7$ cycloalkyl, substituted $C_3-C_7$ cycloalkyl, phenyl, substituted phenyl, naphthyl, thienyl, thiazolidinyl, furyl, pyrrolidino, piperidino, morpholino, or NR$^4$R$^5$, where R$^4$ and R$^5$ are independently $C_1-C_4$ alkyl or R$^4$ and R$^5$ taken together with the nitrogen atom to which they are attached form a pyrrolidino, piperidino or morpholino ring;

or a pharmaceutically acceptable salt thereof, comprising the steps of:

a) reacting a compound of formula IV

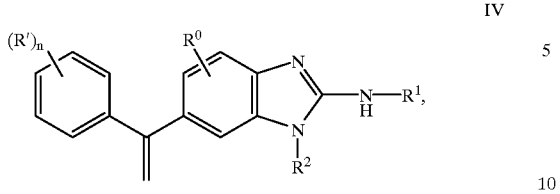

IV wherein R', R⁰, R¹ and R² have the same meaning as above, with between 1.05 and 1.20 equivalents of a brominating reagent in a suitable solvent at a temperature from 10° C. to 30° C. to produce said compound of formula I(d); and b) optionally, salifying said compound of formula I(d) produced in step a).

13. The process of claim 12 wherein said brominating reagent is elemental bromine.

14. The process of claim 13 wherein said reacting step a) is allowed to proceed for between 1 and 3 hours at a temperature of between 20° C. and 25° C.

15. A process for preparing a compound of formula I(e):

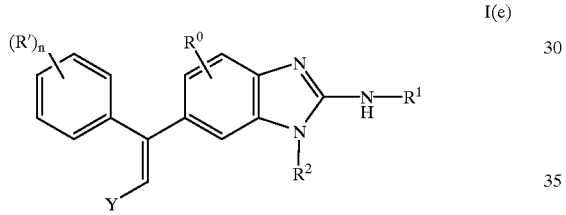

I(e)

wherein

Y is halo;

n is 0, 1, 2, 3, 4 or 5;

R' is independently at each occurrence halo, cyano, cyano ($C_1$–$C_4$)alkyl, amino, halo($C_1$–$C_4$)alkyl, ($C_1$–$C_4$)alkyl amino, di($C_1$–$C_4$)alkylamino, azido, carboxy, $C_1$–$C_6$ alkyl, carbamoyl, carbamoyloxy, carbamoylamino, N-($C_1$–$C_4$)alkylcarbamoyl, —$OCF_3$, $OCCl_3$, $C_1$–$C_4$ alkoxy, $C_1$–$C_4$ alkoxycarbonyl, $C_1$–$C_4$ alkoxycarbonylamino, formyl, $C_2$–$C_4$ alkanoyl, formyloxy, $C_2$–$C_4$ alkanoyloxy, formylamino, $C_2$–$C_4$ alkanoylamino, $C_1$–$C_4$ alkylthio, $C_1$–$C_4$ alkylsulfinyl, $C_1$–$C_4$ alkylsulfonyl, pyrrolidino, piperidino or morpholino;

R⁰ is hydrogen, halo, $C_1$–$C_4$ alkyl, or $C_1$–$C_4$ alkoxy;

R¹ is hydrogen, C(O)($C_1$–$C_6$ alkyl), $SO_2$($C_1$–$C_6$ alkyl); or C(O)$CF_3$; and R² is $C_1$–$C_6$ alkyl, $C_3$–$C_7$ cycloalkyl, halo($C_1$–$C_6$)alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, a group of the formula

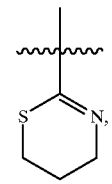

or $SO_2R^3$, where R³ is $C_1$–$C_{10}$ alkyl, halo($C_1$–$C_6$)alkyl, $C_3$–$C_7$ cycloalkyl, substituted $C_3$–$C_7$ cycloalkyl, phenyl, substituted phenyl, naphthyl, thienyl, thiazolidinyl, furyl, pyrrolidino, piperidino, morpholino, or $NR^4R^5$, where R⁴ and R⁵ are independently $C_1$–$C_4$ alkyl or R⁴ and R⁵ taken together with the nitrogen atom to which they are attached form a pyrrolidino, piperidino or morpholino ring;

or a pharmaceutically acceptable salt thereof, comprising the steps of:

a) reacting a compound of formula IV

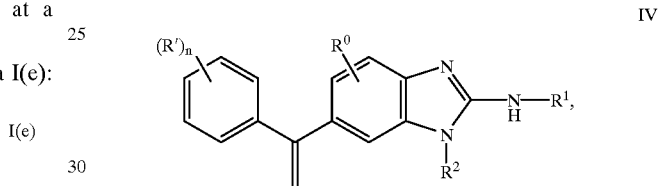

IV wherein R', R⁰, R¹ and R² have the same meaning as above, with between 1.05 and 1.20 equivalents of a brominating reagent in a suitable solvent at a temperature from 10° C. to 30° C. to produce a compound of formula I(d)

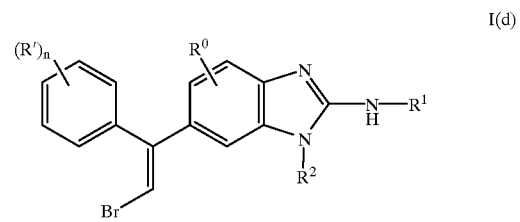

I(d)

wherein R', R⁰, R¹ and R² have the same meaning as defined above;

b) deprotonating said compound of formula I(d) with a kinetic base in a suitable solvent;

c) exposing the product of step b) to a 2° or 3° $C_3$–$C_4$ alkyl lithium;

d) exposing the product of step c) to a halogenating reagent to provide said compound of formula I(e); and e) optionally, salifying said compound of formula I(e) of step d).

16. The process of claim 15 wherein said kinetic base is phenyl lithium and said 2° or 3° $C_3$–$C_6$ alkyl lithium is t-butyl lithium.

17. The process of claim 12 further comprising the step of recrystallizing said compound of formula I(d) from step a) to provide said compound of formula I(d) having an isomeric purity of >99%.

18. A compound represented by structure I(d):

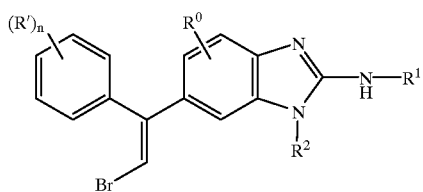

wherein n is 0, 1, 2, 3, 4 or 5;

R' is independently at each occurrence halo, cyano, cyano $(C_1-C_4)$alkyl, amino, halo$(C_1-C_4)$alkyl, $(C_1-C_4)$ alkylamino, di$(C_1-C_4)$alkylamino, azido, carboxy, $C_1-C_6$ alkyl, carbamoyl, carbamoyloxy, carbamoylamino, N-$(C_1-C_4)$alkylcarbamoyl, —OCF$_3$, OCCl$_3$, $C_1-C_4$ alkoxy, $C_1-C_4$ alkoxycarbonyl, $C_1-C_4$ alkoxycarbonylamino, formyl, $C_2-C_4$ alkanoyl, formyloxy, $C_2-C_4$ alkanoyloxy, formylamino, $C_2-C_4$ alkanoylamino, $C_1-C_4$ alkylthio, $C_1-C_4$ alkylsulfinyl, $C_1-C_4$ alkylsulfonyl, pyrrolidino, piperidino or morpholino;

$R^0$ is hydrogen, halo, $C_1-C_4$ alkyl, or $C_1-C_4$ alkoxy;

$R^1$ is hydrogen, C(O)($C_1-C_6$ alkyl), SO$_2$($C_1-C_6$ alkyl); or C(O)CF$_3$; and $R^2$ is $C_1-C_6$ alkyl, $C_3-C_7$ cycloalkyl, halo$(C_1-C_6)$alkyl, phenyl, substituted phenyl, furyl, thienyl, thiazol-2-yl, 2-acetamido-4-methyl-thiazol-5-yl, 1,3,4-thiadiazol-2-yl, 2-methyl-1,3,4-thiadiazol-5-yl, 2-methylamino-1,3,4-thiadiazol-5-yl, a group of the formula

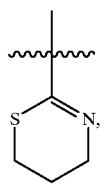

or SO$_2$R$^3$, where R$^3$ is $C_1-C_{10}$ alkyl, halo$(C_1-C_6)$alkyl, $C_3-C_7$ cycloalkyl, substituted $C_3-C_7$ cycloalkyl, phenyl, substituted phenyl, naphthyl, thienyl, thiazolidinyl, furyl, pyrrolidino, piperidino, morpholino, or NR$^4$R$^5$, where R$^4$ and R$^5$ are independently $C_1-C_4$ alkyl or R$^4$ and R$^5$ taken together with the nitrogen atom to which they are attached form a pyrrolidino, piperidino or morpholino ring;

or a pharmaceutically acceptable salt thereof; prepared by a process comprising the steps of:

a) reacting a compound of formula IV

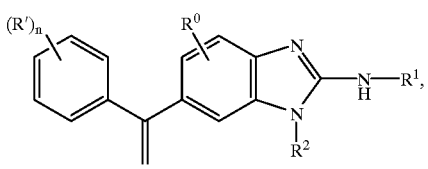

wherein R', $R^0$, $R^1$ and $R^2$ have the same meaning as above, with between 1.05 and 1.20 equivalents of a brominating reagent in a suitable solvent at a temperature above 10° C. to produce said compound of formula I(d);

b) recrystallizing said compound of formula I(d) produced in step a) to provide an isomeric purity>99%; and c) optionally, salifying said compound of formula I(d) produced in step b).

19. The compound of claim 18 wherein said compound of formula IV in step a) is reacted with between 1.05 and 1.15 equivalents of said brominating reagent at a temperature between 20° and 30° C.

20. The compound of claim 18 wherein said suitable solvent in step a) is a mixture of tetrahydrofuran and carbon tetrachloride.

* * * * *